United States Patent [19]

Baldwin et al.

[11] Patent Number: 5,216,020
[45] Date of Patent: Jun. 1, 1993

[54] SUBSTITUTED 4,5-DIHYDROTHIENO(2,3-B)THIOPHENE-2-SULFONAMIDES AND 6,6-DIOXIDES THEREOF

[75] Inventors: John J. Baldwin, Gwynedd Valley; Kenneth L. Shepard, North Wales; Ronald J. Hudcosky, Perkasie; Theresa M. Williams, Harleysville, all of Pa.

[73] Assignee: Merck & Co., Inc., Rahway, N.J.

[21] Appl. No.: 742,988

[22] Filed: Aug. 9, 1991

Related U.S. Application Data

[63] Continuation-in-part of Ser. No. 596,831, Oct. 12, 1990, abandoned.

[51] Int. Cl.$^5$ .................... A61K 31/38; C07D 495/04
[52] U.S. Cl. ........................... 514/443; 514/233.8; 514/409; 544/145; 548/409; 548/410; 591/50
[58] Field of Search ............... 549/50; 514/443, 233.8; 544/145

[56] References Cited

U.S. PATENT DOCUMENTS

| 4,386,098 | 5/1983 | Woltersdorf, Jr. et al. | 514/367 |
| 4,416,890 | 11/1983 | Woltersdorf, Jr. | 514/367 |
| 4,426,388 | 1/1984 | Woltersdorf, Jr. | 514/367 |
| 4,585,787 | 4/1986 | Shepard | 514/445 |
| 4,668,697 | 5/1987 | Shepard et al. | 514/445 |
| 4,677,115 | 6/1987 | Baldwin et al. | 514/432 |
| 4,797,413 | 6/1987 | Baldwin et al. | 514/432 |
| 4,876,271 | 10/1989 | Hartman et al. | 514/443 |
| 4,894,390 | 1/1990 | Hartman et al. | 514/443 |
| 4,929,549 | 5/1990 | Hartman et al. | 549/50 |
| 5,045,561 | 9/1991 | Baldwin et al. | 514/432 |

FOREIGN PATENT DOCUMENTS

| 296879 | 12/1988 | European Pat. Off. . |
| 307084 | 3/1989 | European Pat. Off. . |
| 382537 | 8/1990 | European Pat. Off. . |

*Primary Examiner*—Allen J. Robinson
*Assistant Examiner*—Mark W. Russell
*Attorney, Agent, or Firm*—William H. Nicholson, Joseph F. DiPrima

[57] ABSTRACT

Substituted 4,5-dihydrothieno[2,3-b]thiophene-2-sulfonamides and 6,6-dioxides thereof are topically effective carbonic anhydrase inhibitors useful in the treatment of ocular hypertension and glaucoma associated therewith.

8 Claims, No Drawings

SUBSTITUTED 4,5-DIHYDROTHIENO(2,3-B)THIOPHENE-2-SULFONAMIDES AND 6,6-DIOXIDES THEREOF

This patent application is a continuation-in-part of our copending U.S. patent application Ser. No. 596,831 filed Oct. 12, 1990, now abandoned.

SUMMARY OF THE INVENTION

This invention relates to novel derivatives of 4,5-dihydrothieno[2,3-b]thiophene-2-sulfonamides and the 6,6-dioxides of structural formula:

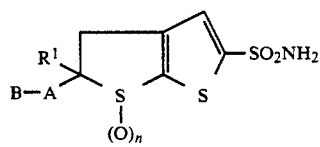

or an ophthalmologically acceptable salt thereof wherein n is 0, 1 or 2, and A and B are as hereinafter defined.

This invention also relates to ophthalmic formulations comprising at least one of the novel compounds as active ingredient either alone or in combination with other ophthalmic medicaments such as pilocarpine, timolol or enaliprilat.

The invention also relates to a method of treating ocular hypertension and glaucoma associated therewith which comprises the topical ocular administration of a novel compound of this invention to a patient in need of such treatment.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. Benzothiophene-2-sulfonamides, benzenesulfonylthiophene-2-sulfonamides, and thieno[2,3-b]thiopyran-2-sulfonamides are also reported to be carbonic anhydrase inhibitors topically effective in reducing intraocular pressure in U.S. Pat. Nos. 4,668,697; 4,585,787; and 4,797,413 respectively.

DETAILED DESCRIPTION OF THE INVENTION

The novel compounds of this invention have structural formula:

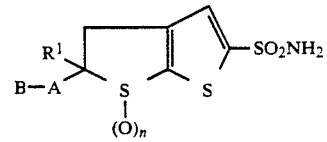

or the (R) or (S) enantiomer or mixture thereof, or an ophthalmologically acceptable salt thereof wherein:
n is 0, 1 or 2, preferably 2;
$R^1$ is
  1) hydrogen,
  2) $C_{1-6}$alkyl, or
  3) $C_{2-6}$alkenyl;
A is —CH$_2$— or —CO—;
B is —OR$^6$ or —NR$^2$R$^3$ wherein
  $R^2$ is hydrogen or $C_{1-6}$alkyl;
  $R^3$ is hydrogen, or $R^6$,
  $R^6$ is
    1) $C_{1-6}$alkyl,
    2) $C_{2-6}$alkenyl,
    3) $C_{2-6}$alkynyl,
    4) $C_{1-6}$alkoxy-$C_{1-6}$alkyl or
    5) $C_{1-6}$alkylthio-$C_{1-6}$alkyl or
    6) $R^4R^5$N-$C_{2-6}$alkyl wherein $R^4$ and $R^5$ are independently hydrogen or $C_{1-6}$alkyl or joined together represent with the nitrogen to which they are attached, a 5-7 membered heterocycle comprising up to one additional hetero atom selected from O, S and N, such as pyrrolidin-1-yl, piperidin-1-yl, morpholin-1-yl, piperazin-1-yl, 4-($C_{1-3}$alkyl)piperazin-1-yl; or
$R^2$ and $R^3$ joined together represent with the nitrogen to which they are attached, a 5-7 membered heterocycle comprising up to one additional hetero atom selected from O, S and N such as pyrrolidin-1-yl, piperidin-1-yl, morpholin-4-yl, piperazin-1-yl, 4-($C_{1-3}$alkyl)-piperazin-1-yl; and $R^1$ and $R^2$ joined together represent a spiro-heterocycle of 5–7 members, preferably 5 members, such as pyrolidinyl.

It is preferred that A be —$CH_2$— and that B be —$NR^2R^3$, and that R' be —$CH_3$, —$C_2H_5$, —$C_3H_7$. It is also preferred that the novel compounds have the (R)-configuration which usually are dextrorotatory.

The terms "alkyl" and "alkoxy" as used herein are meant to include: straight chain alkyl and alkoxy; branched chain alkyl and alkoxy; and $C_{3-6}$cycloalkyl and $C_{3-6}$cycloalkoxy.

A novel process for preparing the compounds of this invention is depicted in Reaction Scheme I.

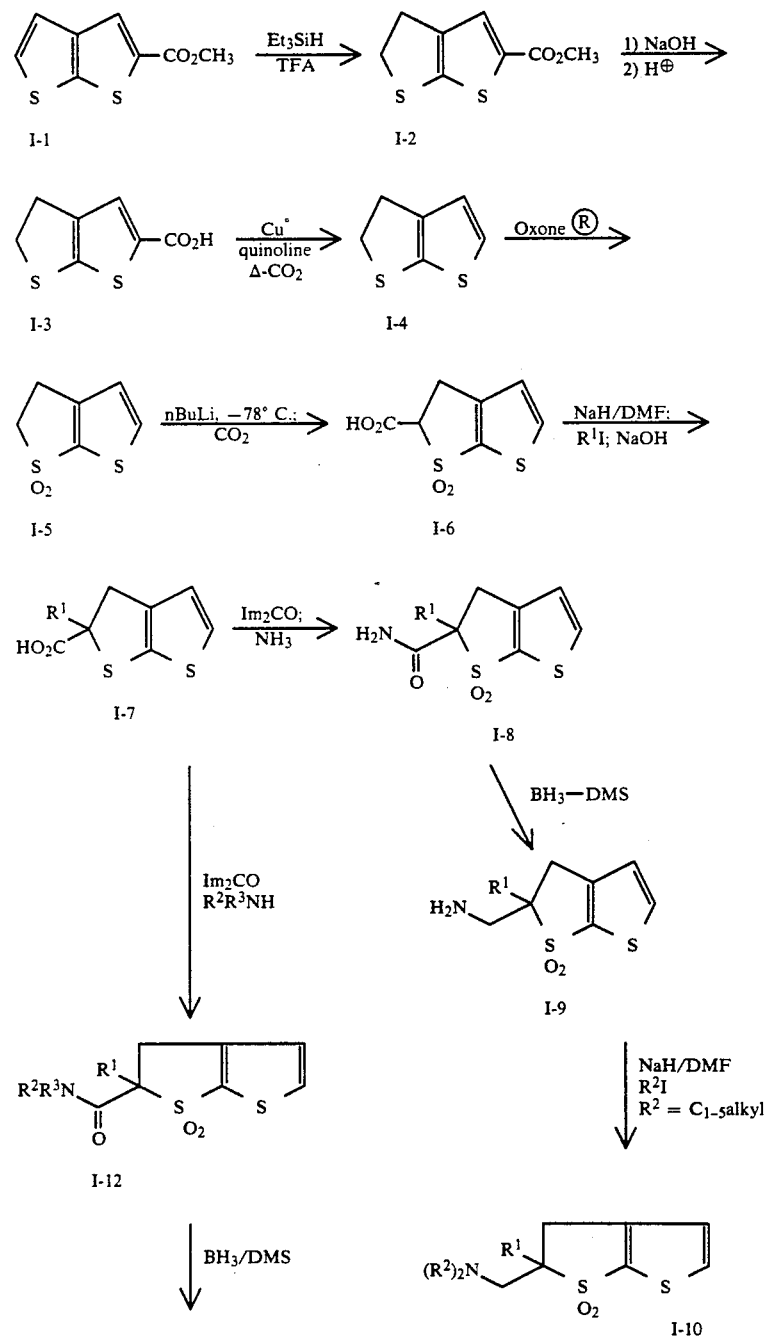

REACTION SCHEME I -continued

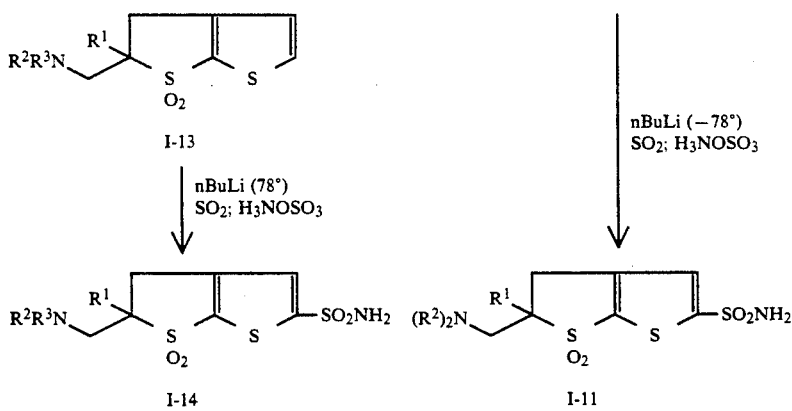

In Reaction Scheme I, Compound I-1 is partially hydrogenated by treatment with excess triethylsilane in an inert atmosphere followed by dropwise addition of a strong acid such as trifluoroacetic acid. After about 10-30 minutes, the mixture is cooled to about −10° to +10° C. and treated with concentrated sulfuric acid (one mole/mole I-1) dropwise. The reduced compound I-2 is isolated by concentration in vacuo to leave the crude material.

The ester group of I-2, which is exemplified as the methyl ester although any lower alkyl ester would do as it is not critical, is removed by saponification with an aqueous solution of an alkali metal hydroxide in THF at or about room temperature for about 5 to 20 hours. The product, I-3 is isolated by acidification and extraction procedures.

Compound I-3 is decarboxylated to form I-4 by heating at about 185° in quinoline in the presence of copper dust until gas evolution ceases.

The dioxide, I-5 is formed by treatment of I-4 with Oxone® at or about room temperature in aqueous lower alcohol such as methanol or ethanol.

Treatment of the dioxide I-5 with n-butyl lithium dropwise in an ethereal solvent such as THF, diethyl ether, 1,2-dimethoxyethane or the like at about −85° to −75° C. over about an hour in an inert atmosphere followed by treatment with carbon dioxide yields the 2-carboxy-1,1-dioxide, I-6.

Compound I-6 is alkylated on the 2-position to form I-7 by dropwise addition to a mixture of a strong base such as sodium hydride and a $C_{1-3}$alkyl iodide in DMF at about 0° C. in an inert atmosphere. After about 1.5 to 5 hours at 0° C., the reaction is quenched with water and alkali is added to saponify the $C_{1-3}$alkyl ester formed during the procedure.

The carboxyl group of I-7 is converted to the amide of I-8 or I-12 by treatment of I-7 with carbonyldiimidazole in an inert atmosphere at about room temperature for one to two hours followed by treatment with a chloroform solution of an excess of ammonia or an amine of formula $R^2R^3NH$ respectively. After 1-2 hours the reaction is quenched with water.

Reduction of the amide of I-8 or I-12 is accomplished by treatment with borane-dimethylsulfide complex in an ethereal solvent such as THF, diethylether, 1,2-dimethoxyethane or the like at about reflux temperature for about 1-3 hours in an inert atmosphere. The reaction is quenched by slow addition of diluted HCl at about 0°-20° C.

The primary amine of I-9 is alkylated to form I-10 by treating I-9 in DMF with sodium hydride and an excess of $C_{1-5}$alkyl iodide at about 0° C. to room temperature over a period of about 2 to 5 hours.

Compounds I-10 and I-13 are converted to the 2-sulfonamide by treatment with n-butyl lithium, sulfur dioxide and hydroxylamine-o-sulfonic acid forming the products I-11 and I-14.

An alternate process for preparing the novel compounds of this invention is depicted in Reaction Scheme II.

REACTION SCHEME II

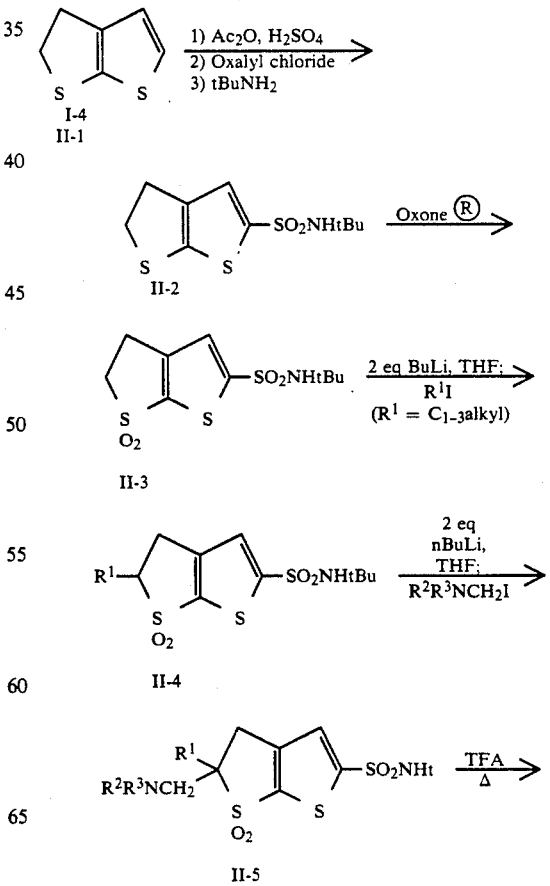

-continued
REACTION SCHEME II

II-6

The first step is the formation of the N-t-butylsulfonamide II-2 by adding the parent molecule II-1 to a mixture of acetic anhydride and sulfuric acid in ethyl acetate or chloroform, at about 0° C. and stirring about 5-20 hours at ambient temperature. After cooling to about 0° C. the mixture is treated dropwise with potassium acetate in a minimum of ethanol, followed after about an hour by isolation of solid sulfonate salt. The sulfonate salt is then added to a mixture of ethyl acetate, oxalyl chloride and DMF at about 0° C. and stirring is continued from 5 to about 20 hours. The reaction is quenched with brine. The sulfonyl chloride thus obtained is treated with t-butylamine.

Oxidation of the sulfur of II-2 to the sulfone II-3 is accomplished as described in Scheme I in the preparation of I-5.

Alkylation to form II-4 and subsequently II-5 is performed by treatment of the respective starting materials in THF or similar solvent with tetramethylethylenediamine, cooling to dry ice temperature and treating with n-butyl lithium, and then with the appropriate alkyl iodide. After warming to room temperature over about 3-6 hours the reaction is quenched by addition of water.

The ultimate compound II-6 is prepared by removal of the N-t-butyl group by heating at about 75°-100° C. in trifluoroacetic acid in an inert atmosphere for about 1 to 4 hours. The excess TFA is evaporated in vacuo and the residue is neutralized with aqueous alkali.

A third novel process, Reaction Scheme III depicts the synthesis of a chiral intermediate and its conversion to optically pure final products:

REACTION SCHEME III

III-1

III-2

III-3
I-5

-continued
REACTION SCHEME III

III-4

III-5

III-6

III-7a = high $R_f$ diastereomer
III-7b = low $R_f$ diastereomer

III-8a = (−)isomer
III-8b = (+)isomer

III-9a = (−)isomer
III-9b = (+)isomer

.HCl

III-10a = (+)isomer
III-10b = (−)isomer

Compound III-1 is oxidized with Oxone ® to form the dioxide by the procedure described for the oxidation of II-2, form III-2 followed by decarboxylation with Cu/quinoline to III-3, carboxylation to III-4, alkylation at the 5-position to form III-5 and converted to III-6 by a series of process steps, each of which is described in the previous Reaction Schemes I and II. The diastereomeric amides III-7 are prepared by condensation of the carboxylic acid III-6 and L-phenylalanine ester by treatment with 1-(3-dimethylaminopropyl)-3-ethylcarbodiimide (EDC) and 1-hydroxybenzotriazole at about pH 8 in DMF, chloroform or the like at about 15° to 25° C. for about 1-5 hours. The diastereomers are separated by column chromatography on silica gel eluting with ethyl acetate/hexane.

Each diastereomer in turn is converted to the optically active carboxylic acid, III-8, by hydrolysis with strong acid such as 6N hydrochloric by heating at 85° C. to reflux temperature for about 5 to 10 hours.

The amides III-9(a) and (b) are prepared by treating the respective carboxylic acid III-8(a) and (b) with BOP-reagent in DMF at about 15°-25° C. for about 10-30 minutes followed by addition to an amine, $R^2R^3NH$ in a chlorinated hydrocarbon such as chloroform or methylene chloride for about 15 minutes to 1 hour.

Reduction to the final products III-10(a) and (b) proceeds as described for I-12 to I-13 described above.

A process for preparing the 6-spiro compounds is depicted in Reaction Scheme IV:

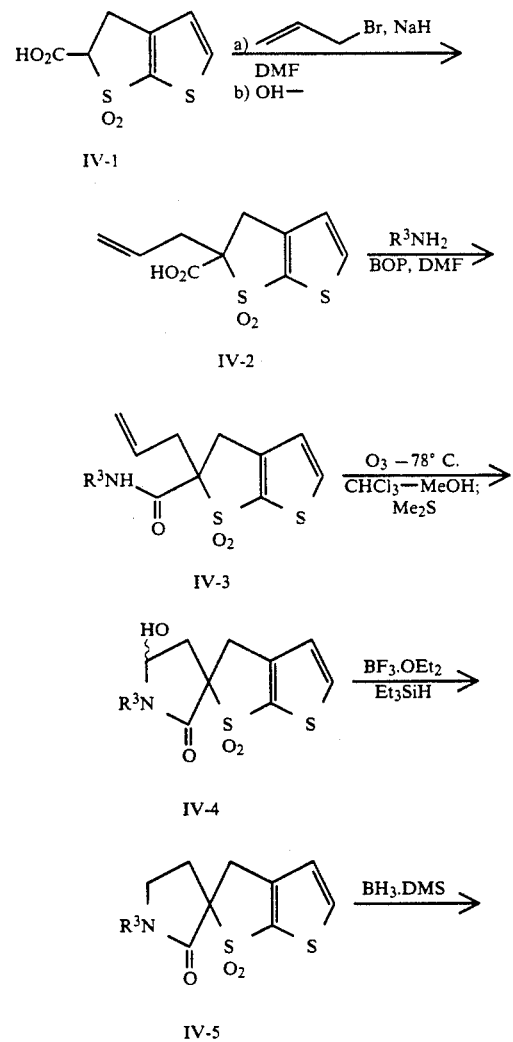

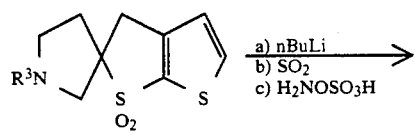

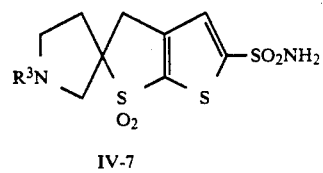

Treatment of IV-1 with sodium hydride and allyl bromide in DMF at about 15° to 25° C. for about 10-20 hours yields the 6-allyl compound, IV-2.

Compound IV-2 is converted to the N-$C_{1-3}$alkyl-amide, IV-3 by treatment with BOP reagent at or aobut 0° C. followed by slow addition of a large excess of alkylamine and stirring for about 1-3 hours after addition is complete.

Treatment of IV-3 with ozone at about −80° C. in methanol/chloroform until a pale blue color persists converts the 5-allyl group to the 5-formylmethyl group which is in equilibrium with the spiropyrrolidinone, IV-4.

Reduction of IV-4 with boron trifluoride etherate and triethyl silane in a chlorinated hydrocarbon such as chloroform at about 0° C. over about 2 to 8 hours yields the pyrrolidinone, IV-5.

Further reduction with borane dimethyl sulfide complex in an ethereal solvent such as THF, diethyl ether or the like at about 15°-25° C. followed by heating at or about reflux for about 10-20 hours converts the pyrrolidinone IV-5 to the pyrrolidine, IV-6.

Formation of the sulfonamide group of IV-7 is conducted as described above for preparation of III-6, I-11 and I-14.

The novel pharmaceutical formulations of this invention can be adapted for oral administration such as tablets, capsules or the like; for nasal administration, especially in the form of a spray; for injection, in the form of a sterile injectable liquid; or for topical ocular administration in the form of solutions, suspensions, ointments, solid water soluble polymeric inserts, or gels.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this inventions either alone or in combination with a β-adrenergic blocking agent such as timolol maleate or a parasympathomimetic agent such as pilocarpine. In such combinations the two active agents are present in approximately pharmacologically equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

4,5-Dihydro-5-N,N-dimethylaminomethyl-5-methyl-thieno[2,3-b]-thiophene-2-sulfonamide-6,6-dioxide

Step A: Preparation of Methyl 4,5-dihydrothieno[2,3-b]thiophene-2-carboxylate

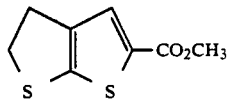

Under nitrogen methyl thieno[2,3-b]thiophene-2-carboxylate (10 g, 0.050 mol) was soaked with triethylsilane (23.5 g, 0.202 mol). Trifluoroacetic acid (57.5 g, 0.504 mol) was then added dropwise to give an orange solution. After fifteen minutes the reaction was cooled to 0° C. and sulfuric acid (2.6 mL, 0.0505 mol) was added dropwise. The reaction was allowed to stir to room temperature over night. The voltiles were removed in vacuo to give the title compound (9.5 g) as a dark amber residue.

Step B: Preparation of 4,5-Dihydrothieno[2,3-b]thiophene-2-carboxylic acid

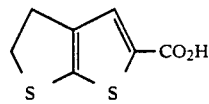

Methyl 4,5-dihydrothieno[2,3-b]thiophene-2-carboxylate (9.5 g, 50 mmol) was dissolved in 200 mL THF followed by treatment with 100 mL of 20% sodium hydroxide and stirred overnight. THF was removed in vacuo to give a dark residue. The residue was taken up in water and extracted with ethyl acetate two times. The aqueous phase was then acidified to pH<1 with conc. HCl and extracted 3×200 mL ethyl acetate. The combined extracts were washed with: 1× water, 2× brine followed by drying over magnesium sulfate. The solution was filtered and the solvent evaporated to give the title compound as a solid (8.1 g). $^1$H NMR (300 MHz,DMSO-d$_6$) d 2.5(t,2H), 2.8(t,2H), 7.5(s,1H), 12.8(bs,1H exch).

Step C: Preparation of 2,3-Dihydrothieno[2,3-b]thiophene

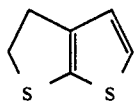

4,5-Dihydrothieno[2,3-b]thiophene-2-carboxylic acid (8.1 g, 43.5 mmol) and copper dust (2.7 g, 43.5 mmol) were combined in 100 mL of quinoline. The reaction was heated to 185° C. internal temperature at which point gas evolution commenced. After about 1 hour the reaction was cooled to room temperature and diluted with ethyl acetate. The mixture was then filtered through celite which was washed well with ethyl acetate. The organic solution was washed 4×100 mL 6N HCl, 2× water, 2× brine then dried over magnesium sulfate. The solution was filtered and the solvent evaporated to give the title compound (6.4 g) as an oil. $^1$H NMR (300 MHz,DMSO-d$_6$) 3.0(t,2H), 3.85(t,2H), 6.9(d,1H), 7.25(d,1H).

Step D: Preparation of 2,3-Dihydrothieno[2,3-b]thiophene-1,1-dioxide

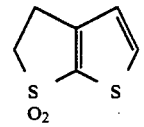

A solution of Oxone ® (570 g, 0.92 mol) in H$_2$O (2 L) was added to a stirred solution of 2,3-dihydrothieno[2,3-b]thiophene (44 g, 0.31 mol) in methanol (1 L). The reaction was stirred for 1.5 h at room temperature, and then extracted with ethyl acetate (5×1 L). The combined extracts were washed with brine, dried over MgSO$_4$, filtered, and concentrated in vacuo to give a soft solid. This was treated with n-butyl chloride and filtered to give the title compound as a light tan solid (35 g, 65%). $^1$H NMR (300 MHz,DMSO-d$_6$) 3.30(2H,t), 3.95(2H,t), 7.10(1H,d), 8.05(1H,d).

Step E: Preparation of 2,3-Dihydrothieno[2,3-b]thiophene-2-carboxylic acid-1,1-dioxide

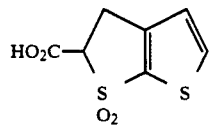

2,3-Dihydrothieno[2,3-b]-thiophene-2-carboxylic acid-1,1-dioxide (35.57 g, 0.204 mol) in THF (300 ml) was cooled to −78° C. under a nitrogen atmosphere. A solution of n-BuLi in hexane (82.7 ml, 2.47M) was added dropwise over a period of 1 h. The dark red solution was stirred for an additional 15 min and then poured over dry ice (2 L) in ether (2 L). The reaction was allowed to warm to room temperature, and the product partitioned between aqueous NaOH and ether. The aqueous phase was extracted twice with ethyl acetate, then made acidic (pH<1) with concentrated HCl. The resulting yellow suspension was extracted into ethyl acetate. The ethyl acetate solution was washed with saturated brine and dried over MgSO$_4$. The solution was filtered and the solvent removed in vacuo to provide two products, an 8:2 mixture of carboxylic acids, as a yellow solid. The solid was triturated with 5% CH$_3$CN in ether and collected by filtration. This was repeated a total of four times to remove most of the undesired minor product carboxylic acid. The resulting light tan powder was dried in a vacuum oven at 20° C. under house vacuum overnight to provide the title compound (21.3 g, 47%) mp=189°-193° C. (singes 165° C.). The filtrates from the washings were combined and the solvent removed in vacuo to give an approximately 1:1 mixture of carboxylic acids (17.6 g, 39%), which could be separated by column chromatography on silica gel with 10% acetic acid in CHCl$_3$.

Step F: Preparation of 2,3-Dihydrothieno-2-methyl[2,3-b]thiophene-2-carboxylic acid-1,1-dioxide

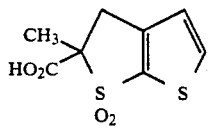

A suspension of NaH (12.3 g, 60% dispersion in oil) in DMF (200 mL, distilled from CaH₂ and degassed) was cooled with stirring to 0° C. under a nitrogen atmosphere. Methyl iodide (18.5 mL, 0.29 mol) was added followed by the dropwise addition of a solution of 2,3-dihydrothieno[2,3-b]thiophene-2-carboxylic acid-1,1-dioxide (21.33 g, 0.0978 mol) in DMF (200 mL) over a period of 1.25 h. The reaction was stirred at 0° C. for an additional 2.25 h, then quenched with water (100 mL) and 40% NaOH (2 mL). The basic reaction mixture was stirred for an additional 1 h at 0° C., until hydrolysis of the methyl ester was complete. Enough 10% HCl was added to adjust the pH to 6, and the DMF was removed in vacuo. The residue was partitioned between ethyl acetate and water. The pH of the aqueous phase was adjusted to 0 with 10% HCl, and the cloudy solution extracted with ethyl acetate (3×500 mL). The volume of ethyl acetate was reduced to 500 mL, and the solution extracted with 10% NaOH (3×300 mL). The aqueous phase was made acidic with concentrated HCl and extracted with two 400 mL portions of ethyl acetate. The combined organic extracts were washed with saturated brine, dried over MgSO₄, and filtered. The solvent was removed in vacuo to give an oil which solidified. The solid was triturated with cold CH₂Cl₂ (50 mL), filtered and dried in vacuo (0.5 mm, 40° C.) to give the title compound as a light tan powder (14.7 g, 65%).

Step G: Preparation of 2,3-Dihydro-2-methylthieno[2,3-b]thiophene-2-carboxamide-1,1-dioxide

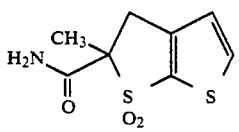

Carbonyldiimidazole (13.3 g, 82.0 mmol) was added to a solution of 2,3-dihydro-2-methylthieno[2,3-b]thiophene-2-carboxylic acid-1,1-dioxide (12.7 g, 54.7 mmol) in dry, degassed DMF (200 mL). The reaction was stirred under N₂ until an aliquot quenched with methanol showed no more starting material by tlc (about 1 h). An excess of a saturated solution of NH₃(g) in CHCl₃ was added and the reaction stirred 1.5 h. The reaction was diluted with water and extracted with ethyl acetate 3X. The combined organic extracts were washed with brine and dried over MgSO₄, filtered, and the solvent removed in vacuo to give a semi-solid. This semi-solid was treated with dichloroethane, cooled in the freezer, and filtered to give the title compound (6.69 g, 53%). ¹H NMR (300 MHz,DMSO-d₆) 1.70(s,3H), 3.00(d, 1H), 3.85(d,1H), 7.10(d,1H), 7.63(bs,1H exch.), 7.69(bs,1H, exch.), 8.05(d,1H).

Step H: Preparation of 2-Aminomethyl-2,3-dihydro-2-methylthieno[2,3-b]thiophene-1,1-dioxide

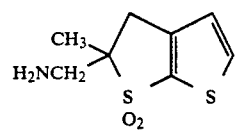

Borane-dimethylsulfide complex (11.12 mL, 10M) was added to a stirred solution of 2,3-dihydro-2-methylthieno[2,3-b]thiophene-2-carboxamide-1,1-dioxide (2.57 g, 11.12 mmol) in THF (75 mL) at room temperature. The reaction mixture was refluxed under a nitrogen atmosphere for 1.5 h and then cooled in an ice bath to 10° C. and slowly quenched with 6N HCl. After gas evolution ceased, the acidic solution was refluxed for 2 h. The reaction mixture was cooled to room temperature and extracted twice with ether. The aqueous phase was made alkaline with aqueous NaOH and extracted with ethyl acetate (5×300 mL). The combined ethyl acetate extracts were washed with saturated brine and then dried over MgSO₄. The solution was filtered and the solvent removed in vacuo to give 2-aminomethyl-2,3-dihydro-2-methylthieno[2,3-b]thiophene-1,1-dioxide as an oil (2.2 g, 91%). ¹H NMR (300 MHz,DMSO-d₆) 1.40(s,3H), 2.85-3.00(m,3H), 3.30(d,1H), 7.05(s,1H), 8.05(s,1H).

Step I: Preparation of 2,3-Dihydro-2-N,N-dimethylaminomethyl-2-methylthieno[2,3-b]thiophene-1,1-dioxide

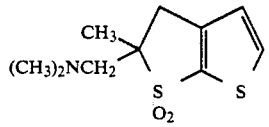

Sodium hydride (1.10 g of a 60% dispersion in oil, 25 mmol) was suspended in dry, degassed DMF (75 mL) under N₂. The stirred suspension was cooled to 0° C. and 2-aminomethyl-2,3-dihydro-2-methylthieno[2,3-b]thiophene-1,1-dioxide (2.2 g, 10.13 mmol) in DMF was added dropwise, followed by methyl iodide (1.26 mL, 20 mmol). The reaction was allowed to warm to room temperature and the progress of the reaction followed by tlc. After 1 h an additional amount of methyl iodide (0.12 mL) was added to drive the reaction to completion. After 2 h the DMF was removed in vacuo and the residue partitioned between ether and 10% HCl. The aqueous phase was washed once more with ether, and then made alkaline (pH>10) by the addition of aqueous sodium hydroxide. The basic solution was extracted with ethyl acetate (3×150 mL) and the combined extracts washed with saturated brine and dried over MgSO₄. The solution was filtered and the solvent removed in vacuo to give the crude product (2.08 g), which was chromatographed on silica gel with ethyl acetate in hexane to give the title compound as an oil (1.57 g, 63%). ¹H NMR (300 MHz,DMSO-d₆) 1.50(s,3H), 2.30(s,6H), 2.65(d,1H), 2.95(d,1H), 3.00(d,1H), 3.15(d,1H), 7.05(d,1H), 8.05(d,1H).

Step J: Preparation of 4,5-Dihydro-5-dimethylamino-5-methylthieno[2,3-b]thiophene-2-sulfonamide-6,6-dioxide hydrochloride

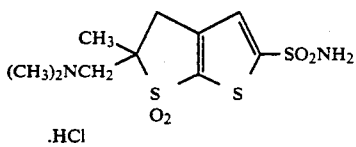

.HCl

A solution of 2,3-dihydro-2-dimethylaminomethyl-2-methylthieno[2,3-b]thiophene-1,1-dioxide (0.90 g, 3.67 mmol) in dry THF (20 mL) was cooled under $N_2$ to −78° C. To this stirred solution n-BuLi (1.62 mL, 2.5M solution in hexane) was added dropwise via syringe. After 30 minutes at −78° C., $SO_2$(g) was condensed into the reaction mixture for several minutes. A white precipitate formed immediately. The reaction was stirred for an additional 10 min. then warmed to room temperature, diluted with ether, and the solid collected. The solid was dissolved in $H_2O$ (250 mL) and sodium acetate (0.75 g, 60.5 mmol) and hydroxylamine-O-sulfonic acid (0.90 g, 60.5 mmol) added. The reaction mixture was stirred overnight at room temperature. The acidic solution was extracted once with ethyl acetate. The pH of the aqueous phase was adjusted to 8 with conc. $NH_4OH$ and extracted twice with an equal volume of ethyl acetate. The combined organic extracts were washed with saturated brine and dried over $MgSO_4$. The solution was filtered and the solvent removed in vacuo to give an oil. This oil was chromatographed on silica gel with methanolchloroform to give the free base of the title compound as a solid. The solid was dissolved in methanol and treated with HCl. The solvent was removed in vacuo and the residue twice taken up in methanol and the solvent evaporated to remove excess HCl. The resultant solid was triturated with methanol-ether and the solid collected and dried 48 h under house vacuum. The title compound was obtained as a white solid (0.600 g, 45%), mp=242°-245° C. Anal. Calc. for $C_{10}H_{16}N_2O_4S_3 \cdot HCl$: C, 33.28; H, 4.75; N, 7.76. Found: C, 33.31; H, 4.79, N, 8.03.

EXAMPLE 2

4,5-Dihydro-5-N,N-Dimethylaminomethyl-5-methyl-thieno[2,3-b]thiophene-2-sulfonamide-6,6-dioxide hydrochloride

Step A: Preparation of 4,5-Dihydrothieno[2,3-b]thiophene-2-N-t-butylsulfonamide

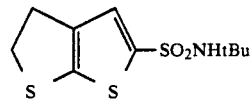

Acetic anhydride (85 g, 0.84 mol) was cooled to 0° C. in 750 mL ethyl acetate. Dropwise sulfuric acid (35.7 mL, 0.643 mol) was introduced, maintaining temperature less than 5° C. After five minutes 2,3-dihydrothieno[2,3-b]thiophene (61 g, 0.42 mol) was added and the reaction stirred overnight. The reaction solution was cooled to 0° C. and potassium acetate (49.4 g, 0.504 mol) in a minimum amount of ethanol added dropwise. After 1 h the suspension of sulfinate salt was collected via vacuum filtration and dried in the collecting funnel. Approximately 2 L of ethyl acetate was cooled to 0° C. and oxalyl chloride (65.2 mL, 0.35 mol) added followed by the dropwise addition of DMF (73.9 mL, 1.07 mol). The reaction was purged with nitrogen for ten minutes, and then the sulfinate salt from above was added. The reaction was stirred overnight. An additional amount of oxalyl chloride (60 mL) and DMF (12 mL) were added to drive the reaction to completion. The mixture was quenched with 500 mL of brine and the two phases separated. The organic layer was washed 1× water, 1× brine, and cooled to about 5° C. t-Butylamine (300 mL) was then quickly added. After 2 h the reaction was acidified with conc. HCl and extracted 3×300 mL ethyl acetate. The extracts were washed 3× water, 2× brine and dried over magnesium sulfate. The solution was filtered free of drying agent and the solvent removed in vacuo to give the title compound as a solid (45 g). H NMR (300 MHz,DMSO-$d_6$) d 1.15(s,9H), 3.15(t,2H), 3.8(t,2H), 7.3(s,1H), 7.6(s,1H exch.).

Step B: Preparation of 4,5-Dihydrothieno[2,3-b]-2-N-t-butylsulfonamide-6,6 dioxide

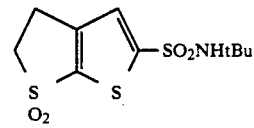

The title compound was prepared in a manner similar to 2,3-dihydrothieno[2,3-b]thiophene-1,1-dioxide. Thus, 4,5-dihydrothieno[2,3-b]thiophene-2-N-t-butylsulfonamide (85 g, 0.30 mol) and Oxone ® (570 g, 0.92 mol) in a total of 5.2 L 1:1 methanol-water gave the title compound as a solid (45 g, 48%). $^1$H NMR (300 MHz-DMSO-$d_6$) 1.20(s,9H), 3.30(t,2H), 3.95(t,2H), 7.55(s,1H), 8.20(s,1H).

Step C: Preparation of 4,5-Dihydro-5-methylthieno[2,3-b]thiophene-2-N-t-butylsulfonamide-6,6-dioxide

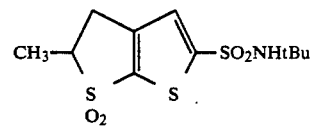

A 1 L three neck flask was fitted with a mechanical stirrer and thermometer, flame dried under vacuum, and a nitrogen atmosphere established. 4,5-Dihydro-thieno[2,3-b]thiophene-2-N-t-butyl-sulfonamide-6,6-dioxide (9.99 g, 32.3 mmol) was placed in the flask and dry THF (290 mL) added. To this solution was added N,N,N',N'-tetramethylethylenediamine (TMEDA) (4.88 mL, 32.3 mmol). The solution was cooled to −78° C. and a solution of n-BuLi (25.08 mL of a 2.58M solution) was added via syringe at such a rate to keep the temperature below −65° C. The total time for the addition was 15 min. The dark red solution began to form a precipitate shortly after addition of BuLi was complete. The reaction was stirred at −78° C. for 45 min and methyl iodide (2.0 mL) in THF (8 mL) was added via syringe. The reaction was allowed to warm slowly to 20° C. over a period of 4 h. The reaction was quenched with water and the THF removed in vacuo. The residue was partitioned between ethyl acetate and 10% aqueous sodium thiosulfate. The organic phase was washed with water and saturated brine, then dried over MgSO$_4$. The solution was filtered and concentrated in vacuo to give an oil which solidified upon standing (11.2 g). This solid was recrystallized from 150 mL n-butylchloride and dried at 65° C. at 0.5 mm for 11 h to give the title compound as yellowish crystals (7.42 g, 71%) mp=143°–144° C. Anal Calc. $C_{11}H_{17}NS_3O_4$: N, 4.33; C, 40.84; H, 5.29. found: N, 4.31; C, 41.14; H, 5.33.

Step D: Preparation of 4,5-Dihydro-5-N,N-dimethylaminomethyl-5-methyl-thieno[2,3-b]thiophene-2-N-t-butylsulfonamide-6,6-dioxide

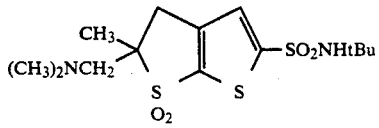

A 500 mL three neck flask was equipped with a magnetic stir bar, nitrogen inlet/outlet, and a serum cap. The apparatus was flame dried under vacuum and a nitrogen atmosphere established. 4,5-Dihydro-5-methylthieno[2,3-b]thiophene-2-N-t-butylsulfonamide-6,6-dioxide (7.2 g, 0.0224 mol) was transfered to the flask followed by dry THF (200 mL). TMEDA (3.37 mL, 0.0224 mol) was added and the stirred solution cooled to −78° C. A solution of n-BuLi in hexane (17.4 mL of a 2.58M solution) was slowly added via syringe, keeping the reaction temperature less than −75° C. The total time for addition was 50 min. The dark red solution was stirred for an additional 25 min and then N,N-dimethylmethyleneammonium iodide (4.14 g, 0.0224 mol, recrystallized from dimethylsulfone) was added portionwise. The reaction was stirred at −78° C. for 1.5 h and the red color gradually discharged during this time. The reaction was allowed to warm to 20° C. over a period of 30 min and water was added. The THF was removed in vacuo and the residue partitioned between ethyl acetate and sodium bicarbonate. The organic phase was washed with water and dried over MgSO$_4$. The solution was filtered and concentrated in vacuo to give 5.2 g of a yellow foam. This was chromatographed on silica gel using 2% methanol in chloroform. The combined fractions of the major product gave the title compound as a yellow foam (3.2 g, 37%).

Step E: Preparation of 4,5-Dihydro-5-N,N-dimethylaminomethyl-5-methyl-thieno[2,3-b]thiophene-2-sulfonamide-6,6-dioxide hydrochloride

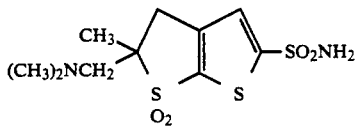

4,5-Dihydro-5-N,N-dimethylaminomethyl-5-methyl-thieno[2,3-b]thiophene-2-N-t-butylsulfonamide-6,6-dioxide was dissolved in trifluroacetic acid (TFA) (40 mL) and heated at 80° C. under N$_2$ for 2 h. The reaction solution was cooled to room temperature and the TFA removed in vacuo. The resulting residue was neutralized with 5% aqueous sodium hydroxide and extracted 2 times with ethyl acetate. The organic phase was washed with saturated brine and dried over MgSO$_4$. The solution was filtered and concentrated in vacuo to give 3.0 g of a white solid, which was chromatographed on silica gel using 10% methanol in chloroform. This gave the free base of the title compound, which was then dissolved in methanol and treated with HCl, and the methanol and excess HCl removed in vacuo. The resulting solid was treated 3 times with methanol, and the solvent removed in vacuo each time. The remaining white solid was dried at 60° C. at 0.5 mm for 18 h to give the title compound (2.7 g, 89%) mp=247°–249° C. Anal. Calc for $C_{10}H_{16}N_2O_4S_3 \cdot HCl$: N, 7.76; C, 33.28; H, 4.75. Found: N, 7.77; C, 33.35; H, 4.70.

EXAMPLE 3

5-Diethylamino-4,5-dihydro-5-methylthieno[2,3-b]thiophene-2-sulfonamide-6,6-dioxide hydrochloride Step A: Preparation of 2-Diethylaminomethyl-2,3-dihydro-2-methylthieno[2,3-b]thiophene-1,1-dioxide

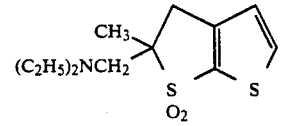

A solution of acetaldehyde (3.85 mL, 69 mmol) and 2-aminomethyl-2,3-dihydro-2-methylthieno[2,3-b]thiophene-1,1-dioxide (1.5 g, 6.9 mmol) in methanol (40 mL) was stirred at room temperature for 10 min. An excess of NaBH$_3$CN was added and the pH of the solution adjusted to 4–5 with methanolic HCl. After several hours the reaction was judged complete by tlc, and the cooled reaction mixture quenched with 6N HCl. When gas evolution had ceased, solvents were removed in vacuo and the residue partitioned between 10% aqueous NH$_4$OH and ethyl acetate. The organic phase was dried over MgSO$_4$, filtered, and the solvent removed in vacuo to give the title compound as an oil (1.5 g, 79%). $^1$H NMR (300 MHz, DMSO-d$_6$) 0.95(t,6H), 1.45(s,3H), 2.60(m,4H), 2.75(d,1H), 2.95(d,2H), 3.20(d,1H), 7.05(d,1H), 8.05(d,1H).

Step B: Preparation of 5-Diethylaminomethyl-4,5-dihydro-5-methylthieno[2,3-b]thiophene-2-sulfonamide-6,6-dioxide hydrochloride

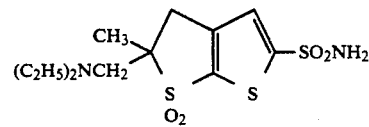

The title compound was prepared in the same way that 4,5-dihydro-5-dimethylaminomethyl-5-methyl-thieno[2,3-b]thiophene-2-sulfonamide-6,6-dioxide hydrochloride was prepared from 2,3-dihydro-2-dimethylaminomethyl-2-methylthieno[2,3-b]thiophene-1,1-dioxide. Thus, 2 N,N-diethylaminomethyl-2,3-dihydro-2-methylthieno[2,3-b]thiophene-1,1-dioxide (1.5 g, 5.49 mmol) gave the free base of the title compound, which was chromatographed on silica gel with 95:5 chloroform-methanol. Conversion to the HCl salt gave the title compound (1.65 g, 85%) mp=179°-182° C. ¹H NMR (300 MHz,DMSO-d₆) 0.95(t,6H), 1.45(s,3H), 2.60(m,4H), 2.75(d,1H), 3.00(m,2H), 3.25(d,1H), 7.55(s,1H), 8.05(bs,2H, exch.). Anal. Calc. for C₁₂H₂₀N₂O₄S₃.HCl: C, 37.05H, 5.44; N, 7.20. Found: C, 36.89; H, 5.59; N, 6.86.

EXAMPLE 4

4,5-Dihydro-5-methyl-5-pyrrolidinomethylthieno[2,3-b]thiophene-2-sulfonamide-6,6-dioxide hydrochloride

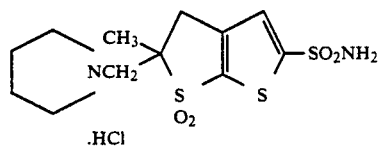

The title compound was prepared in like manner to 4,5-dihydro-5-N,N-dimethylaminomethyl-5-methyl-thieno[2,3-b]thiophene-2-N-t-butylsulfonamide-6,6-dioxide and its subsequent conversion to 4,5-dihydro-5-N,N-dimethylaminomethyl-5-methylthieno[2,3-b]thiophene-2-sulfonamide-6,6-dioxide hydrochloride. Thus, 4,5-dihydro-5-methylthieno[2,3-b]thiophene-2-N-t-butylsulfonamide-6,6-dioxide (6.72 g, 0.0208 mol) and 1-methylenepyrrolidinium chloride (2.48 g, 0.0208 mol) (prepared according to the procedure described in Bohme, H.; Hartke, K. Chem. Ber. (1960) 93, 1305) gave 4,5-dihydro-5-methyl-5-pyrrolidinomethyl-thieno[2,3-b]thiophene-2-N-t-butylsulfonamide-6,6-dioxide, which was refluxed in TFA to give after workup the free base of the title compound as a solid (5.29 g, 73% crude yield). A portion of this was recrystallized from methanol and converted to the HCl salt (965 mg). mp=234°-237° C. Anal Calc. for C₁₂H₁₈N₂O₄S₃.HCl: C, 37.25; H, 4.94; N, 7.24. Found: C, 36.91; H, 4.84; N, 7.17.

EXAMPLE 5

5-(N-Isobutylaminomethyl)-4,5-dihydro-5-methyl-thieno[2,3-b]thiophene-2-sulfonamide-6,6-dioxide hydrochloride Step A: Preparation of 5-(N-t-butylsulfamoyl)-1,1-dioxo-2,3-dihydro-thieno[2,3-b]thiophene-2-carboxylic acid.

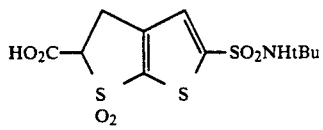

A stirred solution of 4,5-dihydrothieno[2,3-b]thiophene-2-N-t-butylsulfonamide-6,6-dioxide (10 g, 32.3 mmol) and TMEDA (4.87 mL, 32.3 mmol) in dry THF was cooled under N₂ to −78° C. A solution of n-BuLi in hexane (25.0 mL, 2.5M) was added slowly via syringe. The resulting orange suspension was stirred for 30 min and then quenched by blowing a stream of CO₂(g) into the reaction mixture. The reaction was allowed to warm to room temperature, diluted with 6N HCl, and extracted with ethyl acetate. The organic extract was washed with saturated brine and dried over MgSO₄, filtered, and the filtrate concentrated in vacuo to give the title compound as an oil (8.8 g, 78%). ¹H NMR (300 MHz,DMSO-d₆) 1.20(s,9H), 2.25(s,6H), 2.55(m,1H), 2.95(m,2H), 3.40(m,1H), 4.35(m,1H), 7.55(s,1H), 8.15(s,1H,exch.).

Step B: Preparation of Methyl 5-(N-t-butylsulfamoyl)-1,1-dioxo-2,3-dihydro-thieno[2,3-b]thiophene-2-carboxylate.

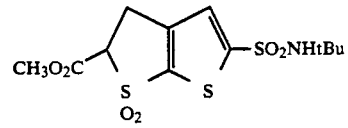

Carbonyldiimidazole (5.3 g, 32.7 mmol) was added at room temperature to a stirred solution of product from Step A (7.7 g, 21.8 mmol) in dry, degassed DMF under an N₂ atmosphere. After 1 h, methanol (150 mL) was added and the reaction stirred for 30 min. The solvents were removed under high vacuum, and the residue taken up in ethyl acetate. This solution was extracted with water and saturated brine, dried over MgSO₄, filtered, and the filtrate evaporated to dryness to give a foam. This foam was treated with n-butyl-chloride and the resulting solid filtered and dried in the air to give the title compound (5.7, 74%). ¹H NMR (300 MHz,DMSO-d₆) 1.20(s,9H), 3.53(d,2H), 3.80(s,3H), 5.30(t,1H), 7.60(s,1H, 8.20(s,1H,exch.).

Step C: Preparation of 5-(N-t-butylsulfamoyl)-1,1-dioxo-2-methyl-2,3-dihydro-thieno[2,3-b]thiophene-2-carboxylic acid.

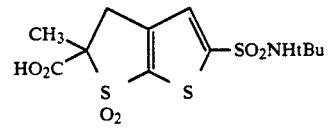

A stirred solution of diisopropylamine (4.44 mL, 31.7 mmol) in THF (200 mL) was cooled to −78° C. under an N₂ atmosphere. A solution of n-butyllithium in hexane (12.3 mL, 2.58M) was added via syringe and the mixture stirred for 10 min at −78° C. and 15 min at 0° C. The mixture was cooled to −78° C. and product from Step B (5.3 g, 14.4 mmol) in THF (50 mL) was added dropwise. The reaction was stirred for 30 min and then methyl iodide (0.94 mL, 15.1 mmol) was added. The reaction was allowed to warm to room temperature overnight, and then quenched with water and 10% aqueous NaOH for 1 h. The DMF was removed in vacuo and water added. The aqueous solution was acidified with 6N HCl and extracted with ethyl acetate. The organic phase was washed with saturated brine and dried over MgSO₄. The solution was filtered and the filtrate freed of solvent to give the title compound (6.25 g, crude product). ¹H NMR (300 MHz,DMSO-d₆) 1.20(s,9H), 1.70(s,3H), 3.17(d,1H), 3.80(d,1H), 7.60(s,1H), 8.20(s,1H,exch.).

Step D: Preparation of 5-(N-Isobutylcarbonyl)-4,5-dihydro-5-methyl-thieno[2,3-b]thiophene-2-N-t-butylsulfonamide-6,6-dioxide

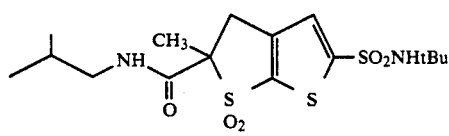

The title compound was prepared in a manner analogous to the preparation of 2,3-dihydro-2-methyl-thieno[2,3-b]thiophene-2-carboxamide. Thus, product from Step C (2.6 g, 6.8 mmol) reacted with carbonyl-diimidazole (2.85 g) and isobutylamine (50 mL) to give the title compound (1.5 g, 60%) after chromatography on silica gel with 6:4 ethyl acetate-hexane. $^1$H NMR (300 MHz,DMSO-$d_6$) 0.80(d,6H), 1.20(s,9H), 1.75(s,3H), 1.80(m,1H), 2.95(m,2H), 3.10(d,1H), 3.90(d,1H), 7.60(s,1H), 8.18(s,1H), 8.23(bt,1H).

Step E: Preparation of 5-(N-Isobutylaminomethyl-4,5-dihydro-5-methyl-thieno[2,3-b]thiophene-2-sulfonamide-6,6-dioxide hydrochloride

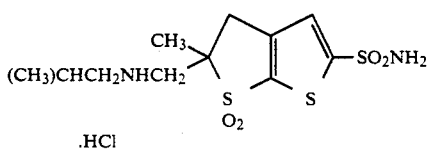

A solution of 5-(N-isobutylcarbamoyl)-4,5-dihydro-5-methylthieno[2,3-b]thiophene-2-N-t-butylsulfonamide-6,6-dioxide (1.5 g, 3.55 mol) in THF (50 mL) was stirred under $N_2$. To this solution was added borane-dimethyl sulfide complex (3.6 mL, 10M) at room temperature. The reaction was refluxed overnight, cooled in an ice bath and quenched with 10% HCl. This solution was refluxed for 30 min, cooled to room temperature, the pH adjusted to 7, and the product extracted into ethyl acetate. The organic extract was washed with brine and dried over $MgSO_4$, filtered and solvent evaporated to give a foam. This foam was dissolved in TFA (40 mL) and heated at 80° C. for 2 h. The reaction was cooled to room temperature and TFA removed in vacuo. The residue was partitioned between 10% HCl and ethyl acetate. The aqueous phase was made neutral with $NH_4OH$ and extracted with ethyl acetate several times. The combined organic extracts were washed with saturated brine, dried over $MgSO_4$, filtered and the filtrate concentrated in vacuo to give the free base of the title compound as a foam (900 mg) which was combined with material obtained in an earlier run (130 mg) and chromatographed on silica gel with chloroform-methanol 95:5. The purified free base was taken up in methanolic HCl, evaporated to dryness, and treated twice with methanol, removing the solvent in vacuo each time. The resulting solid was treated with dichloroethane/methanol 2X and removed by filtration. The solid thus obtained was dried overnight in vacuo. The title compound was obtained as a white solid (458 mg, 33% for the combined two runs), mp=235°–237° C. Anal. Calc. for $C_{12}H_{20}N_2O_4S_3.HCl$: C, 37.05; H, 5.45; N, 7.20. Found: C, 36.70; H, 5.32; N, 7.22.

EXAMPLE 6

5-(N-Ethylaminomethyl)-4,5-dihydro-5-methyl-thieno[2,3-b]thiophene-2-sulfonamide-6,6-dioxide hydrochloride

Step A: Preparation of 5-(N-ethylcarbamoyl 4,5-dihyro-5-methylthieno[2,3-b]thiophene-2-N-t-butyl-sulfonamide-6,6-dioxide

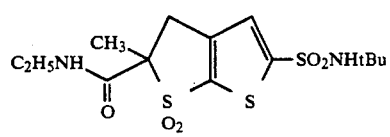

The title compound was prepared in the same way as 2,3-dihydro-2-methylthieno[2,3-b]thiophene-2-carboxamide. Thus, product from Example 5, Step C (2.8 g, 7.6 mmol) reacted with carbonyldiimidazole (2.84 g, 17.5 mmol) and ethylamine (30 mL) in DMF (200 mL) and the crude product chromatographed on silica gel with 1:1 ethyl acetate in hexane to give the title compound as a foam (1.0 g, 33%). $^1$H NMR (300 MHz,DMSO-$d_6$) 1.05(t,3H), 1.20(s,9H), 1.70(s,3H), 3.05(d,1H), 3.15(m,2H), 3.90(d,1H), 7.60(s,1H), 8.20(s,1H), 8.25(bt,1H).

Step B: Preparation of 5-(N-ethylaminomethyl)-4,5-dihydro-5-methyl-thieno[2,3-b]thiophene-2-sulfonamide-6,6-dioxide hydrochloride

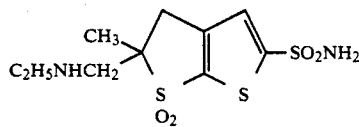

The title compound was prepared in the same way as 5-(N-isobutylaminomethyl)4,5-dihydro-5-methyl-thieno[2,3-b]thiophene-2-sulfonamide-6,6-dioxide hydrochloride. Thus, 5-(N-ethylcarbamoyl)-4,5-dihydro-5-methylthieno[2,3-b]thiophene-2-N-t-butylsulfona-mide-6,6-dioxide (970 mg, 2.46 mmol) gave the title compound (600 mg, 67%) which was recrystallized from dichloroethane and dried under high vacuum to give a solid, mp=228°–230° C. Anal. Calc. for $C_{10}H_{16}N_2O_4S_3.HCl$: C, 33.28; H, 4.75; N, 7.76. Found: C, 33.11; H, 4.68; N, 7.67.

EXAMPLE 7

4,5-Dihydro-5-methyl-5-isopropylaminomethyl-thieno[2,3-b]thiophene-2-sulfonamide-6,6-dioxide hydrochloride

Step A: Preparation of 5-(N-isopropylcarbamoyl)-4,5-dihydro-5-methyl-thieno[2,3-b]thiophene-2-N-t-butylsulfonamide-6,6-dioxide

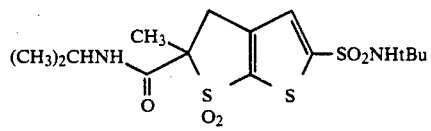

4,5-Dihydro-5-methylthieno[2,3-b]thiophene-2-N-t-butylsulfonamide-6,6-dioxide (5.00 g, 15.43 mmol) was transferred to a flame-dried 500 mL 3 neck round bottomed flask fitted with a thermometer, N₂ inlet/outlet, serum cap and magnetic stir bar. A nitrogen atmosphere was established and dry THF (200 mL) and TMEDA (2.32 mL, 15.43 mmol) transferred to the vessel. The stirred solution was cooled to −78° C. and n-butyllithium (11.9 mL, 2.58M solution in hexane) added slowly via syringe, maintaining a temperature less than −75° C. during the addition (50 min). The dark red reaction was stirred for an additional 20 min and isopropylisocyanate (1.51 mL, 15.43 mmol) was added. The reaction was stirred for 4.5 h at −78° C. and then quenched with water. The solution was warmed to room temperature and THF removed in vacuo. The residue was partitioned between ethyl acetate and 10% HCl. The organic phase was washed with saturated brine, dried over MgSO₄, filtered and concentrated in vacuo to give the crude product (4.5 g). This was chromatographed on silica gel with ethyl acetate in hexane to give a white solid (3.2 g, 51%) which was dried for 36 h at 60°-70° C./0.5 mm. Anal. Calc. for C₁₅H₂₄N₂O₅S₃: C, 44.09; H, 5.92; N, 6.85. Found: C, 44.20; H, 5.87; N, 6.81.

Step B: Preparation of 4,5-dihydro-5-methyl-5-isopropylaminomethyl-thieno[2,3-b]thiophene-2-sulfonamide-6,6-dioxide hydrochloride

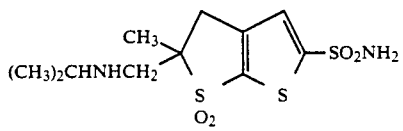

The title compound was prepared in the same way as 5-(N-isobutylaminomethyl)4,5-dihydro-5-methyl-thieno[2,3-b]thiophene-2-sulfonamide-6,6-dioxide hydrochloride. Thus 5-(N-isopropylcarbamoyl)-4,5-dihydro-5-methylthieno[2,3-b]thiophene-2-N-t-butylsulfonamide-6,6-dioxide (3.0 g, 7.3 mmol) was reduced with borane-dimethylsulfide complex (5.0 mL, 50 mmol), deprotected with TFA, and converted to the HCl salt to give the title compound as a white solid (1.32 g, 48% over two steps), mp=132°-135° C. Anal. Calc. for C₁₁H₁₈N₂O₄S₃.HCl.½H₂O: C, 34.41; H, 5.25; N, 7.29. Found: C, 34.42; H, 5.19; N, 7.11.

EXAMPLE 8

4,5-Dihydro-5-N,N-dimethylaminomethyl-5-n-propyl-thieno[2,3-b]thiophene-2-sulfonamide-6,6-dioxide hydrochloride Step A: Preparation of 2,3-dihydro-2-n-propylthieno[2,3-b]thiophene-2-carboxylic acid-1,1-dioxide

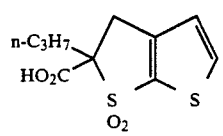

The title compound was prepared in substantially the same way was 2,3-dihydro-2-methylthieno[2,3-b]thiophene-2-carboxylic acid-1,1-dioxide. Thus, 2,3-dihydro-thieno[2,3-b]thiophene-2-carboxylic acid-1,1-dioxide (10.5 g, 0.048 mol) when reacted with NaH (5.76 g, 60% dispersion in oil) and n-propyl iodide (14 mL, 0.047 mol) in DMF (200 mL) gave the title compound as a gum (11.3 g, 90%).

Step B: Preparation of 2,3-dihydro-2-n-propylthieno[2,3-b]thiophene-2-carboxamide-1,1-dioxide

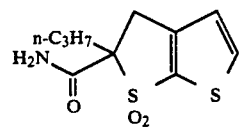

The title compound was prepared in the same way as 2,3-dihydro-2-methylthieno[2,3-b]thiophene-2-carboxamide-1,1-dioxide. Thus, 2,3-dihydro-2-n-propyl-thieno[2,3-b]thiophene-2-carboxylic acid-1,1-dioxide (11.3 g, 43.4 mmol) and carbonyldiimidazole (10.55 g, 65.0 mmol) gave the title compound as a white solid (5.48 g, 48%). ¹H NMR (300 MHz,DMSO-d₆) 1.30(m,2H), 1.90(t,3H), 1.75(m,1H), 2.45(m,1H), 3.1(d,1H), 3.80(d,1H), 7.10(d,1H), 7.65(bd,2H), 8.05(s,1H).

Step C: Preparation of 2-aminomethyl-2,3-dihydro-2-n-propylthieno[2,3-b]thiophene-1,1-dioxide

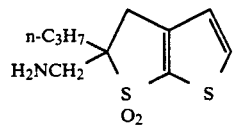

The title compound was prepared substantially the same as 2-aminomethyl-2,3-dihydro-2-methyl-thieno[2,3-b]thiophene-1,1-dioxide. Thus, 2,3-dihydro-2-n-propylthieno[2,3-b]thiophene-2-carboxamide-1,1-dioxide (5.45 g, 21.0 mmol) reacted with borane-dimethyl sulfide complex (21 mL, 10M) to give, after work up, the title compound (4.0 g, 77%). ¹H NMR (300 MHz,DMSO-d₆) 0.95(t,3H), 1.35(m,2H), 1.80(m,1H), 2.00(m,1H), 2.80(d,1H), 2.95(d,1H), 3.10(d,1H), 3.23(d,1H), 7.05(d,1H), 8.05(d,1H).

Step D: Preparation of 2,3-dihydro-2-N,N-dimethylaminomethyl-2-n-propyl-thieno[2,3-b]thiophene-1,1-dioxide

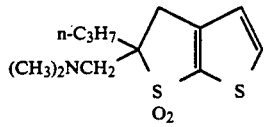

The title compound was prepared in substantially the same way as 2,3-dihydro-2-N,N-dimethylaminomethyl-2-methylthieno[2,3-b]thiophene-1,1-dioxide. Thus, 2-aminomethyl-2,3-dihydro-2-n-propylthieno[2,3-b]thiophene-1,1-dioxide (4.0 g, 16.3 mmol) was N-methylated with methyl iodide (2.53 mL, 40.7 mmol) in DMF/NaH to give the title compound (2.62 g, 60%). ¹H NMR (300 MHz,DMSO-d₆) 0.85(t,3H), 1.35(,.2H), 1.75(m,1H), 1.95(m,1H), 2.25(s,6H), 2.65(d,1H), 2.95(d,1H), 3.05(d,1H), 3.10(d,1H), 7.05(d,1H), 8.05(d,1H).

Step E: Preparation of 4,5-dihydro-5-N,N-dimethylaminomethyl-5-n-propyl-thieno[2,3-b]thiophene-2-sulfonamide-6,6-dioxide hydrochloride

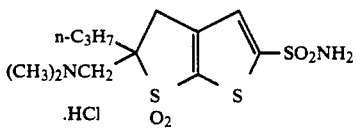

The title compound was prepared in the same way as 4,5-dihydro-5-N,N-dimethylaminomethyl-5-methyl-thieno[2,3-b]thiophene-2-sulfonamide-6,6-dioxide hydrochloride. Thus, 2,3-dihydro-2-N,N-dimethylaminomethyl-2-n-propylthieno[2,3-b]thiophene-1,1-dioxide (2.59 g, 9.47 mmol) gave the free base of the title compound (2.9 g). The free base was converted to the hydrochloride salt to give, after trituration with methanol and drying in vacuo, the title compound (2.3 g, 62%) mp=246°-249° C. Anal. Calc. for $C_{12}H_{20}N_2O_4S_3 \cdot HCl$: C, 37.05; H, 5.46; N, 7.20. Found: C, 37.20; H, 5.60; N, 6.97.

EXAMPLE 9

(+) and (−)-5-(N,N-Dimethylaminomethyl)-5-methyl-4,5-dihydrothieno[2,3-b]thiophene -2-sulfonamide-6,6-dioxide hydrochloride Step A: Preparation of 4,5-dihydrothieno[2,3-b]thiophene-2-carboxylic acid-6,6-dioxide

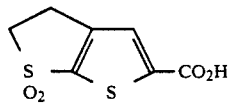

4,5-Dihydrothieno[2,3-b]thiophene-2-carboxylic acid (88.3 g, 0.474 mol) was added to a solution of Oxone ® (730 g, 1.18 mol) in water (3.0 L), and the resulting suspension heated on a steam bath for 1 hour. During this time the solids dissolved to give a clear yellow solution. The reaction was cooled to 60° C. and filtered. The filtrate was extracted four times with ethyl acetate (6 L total) and the combined extracts washed with saturated brine and dried over magnesium sulfate. The solution was filtered and concentrated in vacuo to give the title compound as a yellow solid (70 g, 68%). Recrystallization from dichloroethane gave an off-white powder, mp=227°-230° C. Anal. Calc. for $C_7H_6O_4S_2$: C, 38.52; H, 2.77. Found: C, 38.53; H, 2.61.

Step B: Preparation of 2,3-dihydrothieno[2,3-b]thiophene-1,1-dioxide

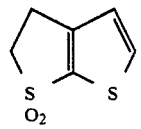

Copper dust (13.4 g. 0.20 mol) was added to a solution of 4,5-dihydrothieno[2,3-b]thiophene-2-carboxylic acid-6,6-dioxide (45 g, 0.20 mol) in quinoline (500 mL) in a reaction vessel fitted with an efficient condenser. The well stirred reaction mixture was heated to 180° C. for 1.5 hours under a nitrogen atmosphere. The dark solution was cooled to room temperature and diluted with ethyl acetate (2 L). The solution was washed with 6N HCl, water, saturated sodium bicarbonate, and saturated brine. The organic phase was dried over magnesium sulfate and treated with decolorizing carbon. Filtration and evaporation of solvent gave the title compound as a solid (33 g, 95%).

Step C: Preparation of 2,3-dihydrothieno[2,3-b]thiophene-2-carboxylic acid-1,1-dioxide

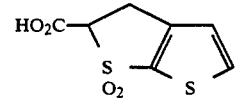

2,3-Dihydrothieno[2,3-b]thiophene-1,1-dioxide (35.5 g, 0.204 mol) in THF (300 mL) was cooled to −78° C. under a nitrogen atmosphere. A solution of n-butyllithium in hexane (82.7 mL, 2.47M) was added dropwise over a period of 1 hour. The dark red solution was stirred for an additional 15 minutes and poured over dry ice (2 L) in ether (2 L). The reaction was allowed to warm to room temperature and the product partitioned between aqueous sodium hydroxide and ether. The aqueous phase was extracted twice with ethyl acetate, then rendered acidic (pH 1) with concentrated HCl. The resulting yellow suspension was extracted into ethyl acetate. The ethyl acetate solution was washed with saturated brine and dried over magnesium sulfate, filtered, and the solvent removed in vacuo to provide an 8:2 mixture of carboxylic acids. The solid was triturated with 5% acetonitrile in ether and collected by filtration. This was repeated a total of four times to remove most of the undesired minor product. The filtrates from the washings were combined to give approximately 1:1 mixture of carboxylic acids (17.6 g, 39%), which could be separated by column chromatography on silica gel with 10% acetic acid in chloroform. The filtered product was a light tan powder which was dried in a vacuum oven at 20° C. under house vacuum overnight to provide the title compound (21.3 g, 47%) in >95% purity.

Step D: Preparation of 2-methyl-2,3-dihydrothieno[2,3-b]thiophene-2-carboxylic acid-1,1-dioxide

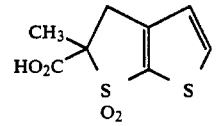

A suspension of sodium hydride (12.3 g, 60% dispersion in oil) in DMF (200 mL, distilled from calcium hydride) was cooled with stirring to 0° C. under a nitrogen atmosphere. Methyl iodide (18.5 mL, 0.29 mol) was added followed by the dropwise addition of 2,3-dihydrothieno[2,3-b]thiophene-2-carboxylic acid-1,1-dioxide (21.33 g. 0.0978 mol) in DMF (200 mL) over a period 1.25 hours. The reaction was stirred at 0° C. for an additional 2.25 hours, then quenched with water (100 mL) and 40% sodium hydroxide (2 mL). The basic solution was stirred for an additional 1 hour at 0° C., until hydrolysis of the ester was complete by tlc. 10% HCl was added to adjust the pH to 6, and the DMF removed in vacuo. The residue was partitioned between ethyl acetate and water. The pH of the aqueous phase was adjusted to 0 with 10% HCl, and the cloudy solution extracted with ethyl acetate (3×500 mL). The volume of ethyl acetate was reduced to 500 mL and extracted with 10% sodium hydroxide (3×300 mL). The aqueous phase was made acidic with concentrated HCl and extracted with two 400 mL portions of ethyl acetate. The combined organic extracts were washed with saturated brine, dried over magnesium sulfate, and filtered. The solvent was removed in vacuo to give an oil which solidified. The solid was triturated with cold methylene chloride (50 mL), filtered and dried in vacuo (0.5 mm, 40° C.) to give the title compound as a light tan powder.

Step E: Preparation of 1,1-dioxo-2-methyl-5-sulfamoyl-2,3-dihydrothieno[2,3-b]thiophene-2-carboxylic acid

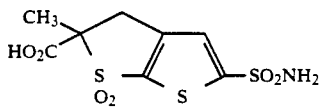

A mechanically stirred solution of 2-methyl-2,3-dihydrothieno[2,3-b]thiophene-2-carboxylic acid-1,1-dioxide (13.9 g, 0.060 mol) in THF (400 mL, dry) was cooled to −78° C. under a nitrogen atmosphere. n-Butyllithium (47.7 mL, 2.5M solution in hexane) was added via syringe at such a rate that the internal temperature remained <−75° C. By the end of the addition (approximately 30 minutes) a very heavy precipitate had formed. The reaction was stirred at −78° C. for 1.25 hours and the sulfur dioxide was condensed into the reaction over a period of 15 minutes. The reaction was stirred for an additional 15 minutes at −78° C. then warmed to room temperature. The solvent was removed in vacuo to give a white solid, which was taken up in dilute sodium hydroxide. The pH was adjusted to 7 with HCl and hydroxylamine-O-sulfonic acid (2 eq, 13 g, 0.119 mol) was added. The clear solution was stirred overnight, and the separated oil extracted with ethyl acetate (2×400 mL). The organic phases were combined and washed with saturated brine and dried over magnesium sulfate. Filtration and evaporation of solvent left a white solid which was triturated with diethyl ether. The product was dried under vacuum to give the title compound as a white solid (14.5 g, 78% yield).

Step F: Preparation of (−) 5(R)-(1(S)-methoxycarbonylphenethylamino)carbonyl-5-methyl-4,5-dihydrothieno[2,3-b]thiophene-2-sulfonamide-6,6-dioxide and (+) 5(S)-(1(S)-methoxycarbonylphenethylamino)carbonyl-5-methyl-4,5-dihydrothieno-[2,3-b]thiophene-2-sulfonamide-6,6-dioxide

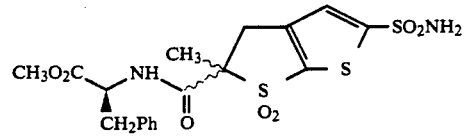

Product from Step E (14.07 g, 0.0452 mol) was dissolved in dry DMF (200 mL, degassed) and L-phenylalanine methyl ester hydrochloride (9.95 g, 0.0452 mol), 1-(3-dimethyl-aminopropyl)-3-ethylcarbodiimide hydrochloride (EDC) (9.5 g, 0.049 mol), and 1-hydroxybenzotriazole (6.11 g, 0.045 mol) added to the stirred solution. Triethylamine was added to adjust the pH to 8. After 2 hours, the reaction was quenched with 10% HCl, and the DMF was removed under high vacuum. The residue was partitioned between 10% HCl and ethyl acetate. The ethyl acetate was extracted with saturated sodium bicarbonate (2 X) and saturated brine, and dried over magnesium sulfate. The solution was filtered and the solvent removed in vacuo to give 22 g of a yellow gum, a mixture of diastereomers. These were separated on a silica gel column (2.5 kg silica gel) with 6:4 ethyl acetate:hexane. The higher $R_f$ component was obtained as a white foam (5.02 g) which was dried at 40° C./0.5 mm Hg. mp=150.0°-150°-5° C. $[\alpha]D^{25}=-64.9$ (c=0.565, CH$_3$OH). Anal. Calc. for $C_{18}H_{20}N_2O_7S_3$: C, 45.75; H, 4.26; N, 5.92. Found: C, 45.87; H, 4.28; N, 5.79. The lower $R_f$ component was obtained as a white foam mp=77°-79° C. $[\alpha]D^{25}=+21.6$ (c=0.480 CH$_3$OH). (3.11 g), Anal. Calc. for $C_{18}H_{20}N_2O_7S_3$: C, 45.75; H, 4.26; N, 5.92. Found: C, 45.97; H, 4.26; N, 5.72. The mixed fractions were combined for rechromatography (6.3g).

Step F Alternate: Preparation of (+)-N-[α-(S)-methoxycarbonyl-α-(4-hydroxyphenethyl)]-2-methyl-1,1,1-dioxo-5-sulfamoyl-2,3-dihydrothieno[2,3-b]thiophene-2-carboxamide and (−)-N-[α-(S)-methoxycarbonyl-α-(4-hydroxyphenethyl)]-2-methyl-1,1,1-dioxo-5-sulfamoyl-2,3-dihydrothieno[2,3-b]thiophene-2-carboxamide

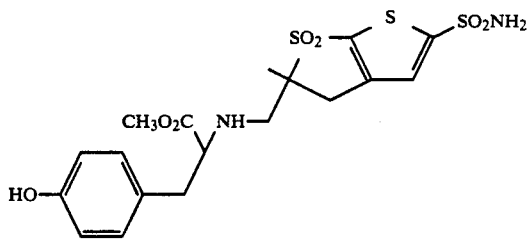

2-Methyl-1,1-dioxo-5-sulfamoyl-2,3-dihydrothieno[2,3-b]thiophene-2-carboxylic acid (2.8 g, 8.99 mmol) was dissolved in freshly degassed anhydrous DMF. To this solution benzotriazol-1-yloxytris-(dimethylamino)phosphonium hexafluorophosphate (5.17 g, 11.7 mmol) was added, followed by L-tyrosine methyl ester (4.39 g, 22.48 mmol). The reaction was stirred for 1½ hours after which time the DMF was removed in vacuo. The resulting residue was partitioned between 6N hydrochloric acid and ethyl acetate. The aqueous layer was separated and its pH adjusted to 7. This neutral mixture was extracted three times with ethyl acetate, and these extracts were combined and washed one time with saturated sodium bicarbonate, followed by one time with brine. After drying with magnesium sulfate and filtration, solvent removal left 6.2 g of foam. The product was purified by medium pressure chromatography (3% CH₃OH in CHCl₃, 50×500 mm column, 230–400 mesh silica gel) to give 400 mg of the (+) title compound: [α]_D = +37° (c=0.76, CH₃OH), mp=189°–190° C.

Anal. Calc'd. for C₁₈H₂₀N₂O₈S₃: C, 44.25; H, 4.12; N, 5.74. Found: C, 44.08; H, 4.04; N, 5.64.

The second component to elute from the column was 1.5 g of the (−) title compound: [α]_D = −49.86° (c=0.55, CH₃OH), mp=107°–110° C.

Anal. Calc'd. for C₁₈H₂₀N₂O₈S₃: C, 44.25; H, 4.12; N, 5.74. Found: C, 43.92; H, 3.92; N, 5.67.

The chromatography also yielded 2.0 g of mixed fractions (80% (+) isomer, 20% (−) isomer).

The subsequent chemistry described in Steps G et seq with the phenylalanine derivative described in Step F is applicable to the tyrosine derivative described in Step F Alternate.

Step G: Preparation of (−) 2(R)-1,1-dioxo-2-methyl-5-sulfamoyl-2,3-dihydrothieno[2,3-b]thiophene-2-carboxylic acid

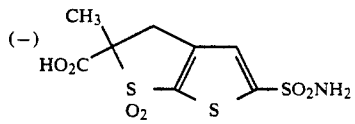

(−) 5(R)-(1(S)-Methoxycarbonylphenethylamino)carbonyl-5-methyl-4,5-dihydrothieno[2,3-b]thiophene-2-sulfonamide-6,6-dioxide (5.02 g, 10.38 mmol) was suspended in 6N HCl (250 mL) and the stirred mixture refluxed for 7 hours. The clear solution was cooled to room temperature and extracted with ethyl acetate (3×250 mL). The combined organic phases were washed with water (5×100 mL), saturated brine and dried over magnesium sulfate. The title compound was obtained as a white solid (3.06 g, 95% yield). Recrystallization from dichloromethane/methanol gave the title compound with mp 229°–230° C.; [α]_D²⁵ −74° (C=1.00, CH₃OH).

Step H: Preparation of (+) 2(R)-1,1-dioxo-2-methyl-5-sulfamoyl-2,3-dihydrothieno[2,3-b]thiophene-2-carboxylic acid.

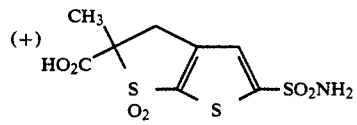

(+) 5(S)-(1(S)-Methoxycarbonylphenethylamino)carbonyl-5-methyl-4,5-dihydrothieno[2,3-b]thiophene-2-sulfonamide-6,6-dioxide (3.03 g, 6.41 mmol) was suspended in 6N HCl (150 mL) and hydrolyzed as described for the (−) isomer. The title compound was obtained as a white solid (2.19 g). [α]D²⁵ = +72.9 (c=0.48, CH₃OH).

Step I: Preparation of (−)-5(R)-(N,N-Dimethylcarbamoyl)-5-methyl-4,5-dihydrothieno[2,3-b]thiophene-2-sulfonamide-6,6-dioxide

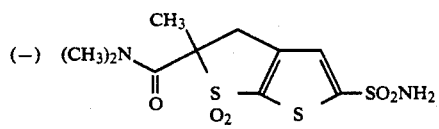

Excess BOP-reagent (3.11 g, 7.04 mmol) was added to a solution of product from Step G (1.82 g, 5.86 mmol) in degassed DMF (200 mL). The reaction was stirred for 20 minutes at room temperature under a nitrogen atmosphere and then transfered via cannula to a dimethylamine-saturated chloroform solution (800 mL) at 0° C. The reaction was stirred an additional 30 minutes, then quenched with water (25 mL). The solvents were removed in vacuo and the residue partitioned between ethyl acetate and water. The organic phase was washed with saturated brine, dried over magnesium sulfate, filtered and concentrated. The crude product was chromatographed on silica gel with 5–10% methanol in chloroform. The title compound was obtained as a foam (1.39 g). A minor product in the reaction eluted subsequent to the title compound, and was identified based on its ¹H nmr spectrum as (−)-5-(N-methylcarbamoyl)-5-methyl-4,5-dihydrothieno[2,3-b]thiophene-2-sulfonamide-6,6-dioxide (228 mg).

Step J: Preparation of (+)-5(S)-(N,N-dimethylcarbamoyl)-5-methyl-4,5-dihydrothieno[2,3-b]thiophene-2-sulfonamide-6,6-dioxide

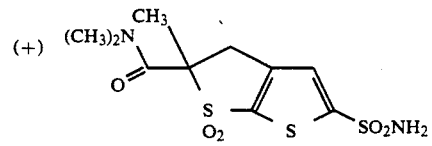

Product from Step H (2.31 g, 7.42 mmol) was reacted with BOP-reagent (3.94 g, 8.91 mmol) and dimethylamine as described for the (−) isomer. Chromatography gave the title compound as a white foam (1.25 g). Also isolated was (+)-5-(N-methylcarbamoyl)-5-methyl-4,5-dihydro-thieno[2,3-b]thiophene-2-sulfonamide-6,6-dioxide (340 mg).

Step K: Preparation of (+)-5(R)-(N,N-dimethylaminomethyl)-5-methyl-4,5-dihydrothieno[2,3-b]thiophene-2-sulfonamide-6,6-dioxide hydrochloride

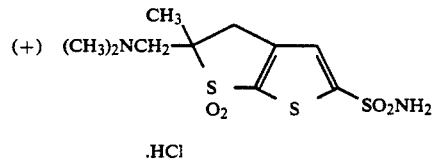

(−)-5(R)-(N,N-Dimethylcarbamoyl)-5-methyl-4,5-dihydrothieno[2,3-b]thiophene-2-sulfonamide-6,6-dioxide (1.34 g, 3.96 mmol) in dry THF (50 mL) was cooled to 0° C. under nitrogen. Borane-dimethyl sulfide complex (4.0 mL, 10M) was added via syringe, and the stirred solution refluxed for 3.5 hours. The reaction was cooled to 0° C. and quenched with 10% HCl. The quenched reaction was refluxed for 1.5 hours. The volatiles were removed in vacuo and the residue partitioned between 10% HCl and ethyl acetate. The ethyl acetate phase contained a reaction by-product, identified by $^1$H nmr by comparison with an authentic sample as 5-hydroxymethyl-5-methyl-4,5-dihydrothieno[2,3-b]thiophene-2-sulfonamide-6,6-dioxide (480 mg after workup). The aqueous phase was neutralized with sodium hydroxide and extracted with ethyl acetate (3 X). The combined organic phases were washed with saturated brine, dried over magnesium sulfate and concentrated to obtain the free base of the title compound as a foam (690 mg, 99% pure by HPLC). The free base was dissolved in methanol and treated with gasseous HCl. Evaporation of methanol (3 X) and drying under high vacuum at 80° C. left the title compound as a white solid (540 mg mp=220°-222° C.; shrinks at 140° C.) which proved to be hygroscopic. $[\alpha]_D^{25} = +16.7$ (c=0.85, methanol). FAB mass spec m/e=325 (m+1). Anal. Calc. for $C_{10}H_{17}O_4S_3N_2Cl$: C, 33.28: H, 4.74; N, 7.76. Found: C, 33.32; H, 4.80; N, 7.79.

Step L: Preparation of (−)-5(S)-(N,N-dimethylaminomethyl)-5-methyl-4,5-dihydrothieno[2,3-b]thiophene-2-sulfonamide-6,6-dioxide hydrochloride

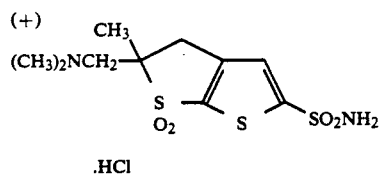

(+)-5(S)-(N,N-Dimethylcarbamoyl)-5-methyl-4,5-dihydrothieno[2,3-b]thiophene-2-sulfonamide-6,6-dioxide (1.25 g, 3.69 mmol) in dry THF (100 mL) was treated with borane-dimethylsulfide complex (3.7 mL, 10M) as described for the (−) isomer. Upon quenching with aq. HCl, the solution was refluxed for only 15 minutes. Workup as described previously and chromatography on silica gel with 7% methanol in chloroform gave the free base of the title compound as a white solid (750 mg). Of this material, 720 mg was converted to the HCl salt and dried in vacuo (70° C., 14 hours). mp=226°-228° C. (shrinks at 140° C.). $[\alpha]_D^{25} = -16.6$ (c=0.885, methanol) Anal. Calc. for $C_{10}H_{17}O_4S_3N_2Cl$: C, 33.28; H, 4.74; N, 7.76. Found: C, 33.45; H, 4.98; N, 7.66.

Employing the procedures substantially as described in Example 9, Steps A-L but substituting the amine $R^2R^3NH$ for the dimethylamine used in Steps I and J, there are produced the enantiomeric products described in Table I:

TABLE I

| $R^1$ | $R^2$ | $R^3$ | $[\alpha]_D^{25}$ |
|---|---|---|---|
| CH$_3$ | CH$_3$OCH$_2$CH$_2$— | H | −3.6 (c—0.66, CH$_3$OH) |
| CH$_3$ | CH$_3$OCH$_2$CH$_2$— | H | +3.3 (c=0.75, CH$_3$OH) |
| CH$_3$ | i-C$_4$H$_9$— | H | +5.1 (c=0.91, CH$_3$OH) |
| CH$_3$ | i-C$_4$H$_9$— | H | −5.1 (c=1.04, CH$_3$OH) |
| | | | $[\alpha]_D^{20}$ |
| CH$_3$ | tetrahydrofuran-2-yl-CH$_2$— | H | +1.9 (c=0.84, CH$_3$OH) |
| CH$_3$ | C$_2$H$_5$SCH$_2$CH$_2$— | H | +4.0 (c=0.83, CH$_3$OH) |
| CH$_3$ | 3-CH$_3$O-C$_6$H$_4$-CH$_2$— | H | +2.8 (c=0.93, CH$_3$OH) |
| CH$_3$ | 3-HO-C$_6$H$_4$-CH$_2$— | H | +5.6 (c=0.94, CH$_3$OH) |

TABLE I-continued

R²R³NCH₂ group substituted structure (see formula)

| R¹ | R² | R³ | |
|---|---|---|---|
| *CH₃ | CH₃OCH₂CH₂OCH₂CH₂— | H | +3.2 (c=1.00, CH₃OH) |

*fumarate (not HCl) salt

Employing the procedures substantially as described in Example 9, Steps A–E, I, J, K and L but substituting for the dimethylamine used in Step I, an approximately equimolar amount of an amine of formula $R^2R^3NH$ there are produced the products described in Table II.

TABLE II

Formula (I): structure with $R^2R^3NCH_2$-, $R_1$, $SO_2NH_2$, $.HCl$

| R¹ | R² | R³ | mp (°C.) |
|---|---|---|---|
| CH₃— | i-C₅H₁₁— | H— | 270–272 |
| CH₃— | CH₃OCH₂CH₂— | H— | 233–235 |
| CH₃— | n-C₃H₇— | H— | 259–261 |
| CH₃— | cyclopropyl-CH₂— | H— | 250–252 |
| CH₃— | CH₃— | H— | 166–170 |
| CH₃— | C₂H₅OCH₂CH₂— | H— | 200–201 |
| C₂H₅— | CH₃OCH₂CH₂— | H— | 207–210 |
| CH₃— | cyclopropyl-CH₂— | CH₃— | 145 |
| CH₃— | CH₃OCH₂CH₂CH₂— | H— | 262 (dec.) |
| CH₃— | CH₃OCH₂CH₂— | CH₃— | 132–133 (free base) |
| C₂H₅ | CH₃— | CH₃ | 242–244 |
| CH₃ | n-C₄H₉— | H | >250 |
| CH₃ | HC≡CCH₂— | H | 163–165 |
| CH₃ | n-C₅H₁₁— | CH₃ | 247–249 |
| CH₃ | CH₃OCH₂CH₂OCH₂CH₂— | H | 170–172 |
| CH₃ | PhCH₂— | H | 140–145 |
| CH₃ | CH₃SCH₂CH₂— | H | 244–246 |

EXAMPLE 10

5-(N-Ethyl-spiro-3'-pyrrolidine)-4,5-dihydrothieno[2,3-b]thiophene-2-sulfonamide hydrochloride.

Step A: Preparation of 2-allyl-2,3-dihydrothieno[2,3-b]thiophene-2-carboxylic acid-1,1-dioxide

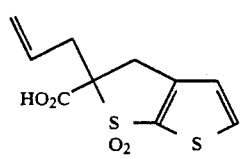

A suspension of sodium hydride (2.57 g 60% dispersion in oil, 0.17 mol) in degassed DMF (200 mL) was stirred under nitrogen at room temperature. To this was added 2,3-dihydrothieno[2,3-b]thiophene-2-carboxylic acid (7.8 g, 0.035 mol) and allyl bromide (9.3 mL, 0.107 mol), and the resulting mixture was stirred overnight. The reaction was cooled to 0° C. and quenched with methanol-water. The quenched reaction was stirred at room temperature for 2 hours. The DMF was removed in vacuo and the residue partitioned between ethyl acetate and aqueous sodium hydroxide. The aqueous phase was rendered acidic with aqueous HCl and extracted 2 times with ethyl acetate. The combined organic phases were washed with brine and dried over magnesium sulfate. The title compound was obtained as an oil (11.1 g).

Step B: Preparation of N-ethyl-2-allyl-2,3-dihydrothieno[2,3-b]thiophene-2-carboxamide-1,1-dioxide

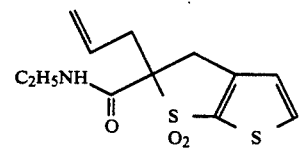

A solution of 2-allyl-2,3-dihydrothieno[2,3-b]thiophene-2-carboxylic acid-1,1-dioxide (8 g, 0.031 mol) and BOP reagent (17.8 g, 0.041 mol) in degassed DMF (150 mL) was cooled to 0° C. under nitrogen. Ethylamine was bubbled into the stirred reaction mixture until the solution was quite basic. After 1.5 hours, the DMF was removed in vacuo and the residue partitioned between ethyl acetate and 6N HCl. The aqueous phase was extracted a total of four times with ethyl acetate and the combined extracts washed with saturated sodium bicarbonate, brine, then dried over magnesium sulfate. Filtration and solvent removal gave the title compound as an oil (7.2 g).

Step C: Preparation of N-ethyl-2-(formylmethyl)-2,3-dihydrothieno[2,3-b]thiophene-2-carboxamide-1,1-dioxide

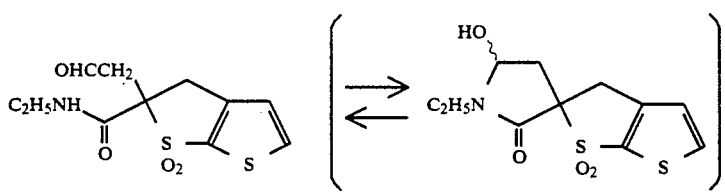

N-Ethyl-2-allyl-2,3-dihydrothieno[2,3-b]thiophene-2-carboxamide-1,1-dioxide (7.2 g, 0.025 mol) in 1:1 methanol-chloroform (300 mL) was cooled to −78° C. Ozone was bubbled into the reaction mixture until a pale blue color persisted. The reaction was sparged with nitrogen for 10 minutes and dimethyl sulfide (7 mL) was added. The solution was warmed to room temperature and the solvents removed in vacuo. The residue was partitioned between water and ethyl acetate. The organic layer was washed with brine and dried over magnesium sulfate. The solution was filtered, and the solvent evaporated to give the title compound as an oil (5.3 g).

Step D: Preparation of 2-(N-ethyl-spiro-3'-pyrrolidinone)-2,3-dihydrothieno[2,3-b]thiophene-1,1-dioxide

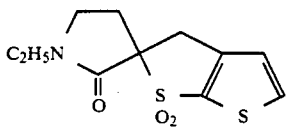

N-Ethyl-2-(formylmethyl)-2,3-dihydrothieno[2,3-b]thiophene-2-carboxamide-1,1-dioxide (5.3 g, 0.018 mol) in chloroform (partially soluble) was cooled to 0° C. and boron trifluoride etherate (4.6 mL, 0.036 mol) and triethylsilane (10 mL, 0.062 mol) added. The reaction was stirred under nitrogen for 5 hours. The reaction was quenched with water and the chloroform removed in vacuo. The remainder was extracted with ethyl acetate (3×100 mL) and the combined organic extracts washed with dilute HCl, sodium bicarbonate and saturated brine, and dried over magnesium sulfate. Evaporation of solvent in vacuo gave the title compound as an oil (4.3 g).

Step E: Preparation of 2-(N-ethyl-spiro-3'-pyrrolidine)-2,3-dihydrothieno[2,3-b]thiophene-1,1-dioxide

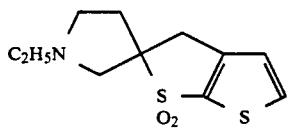

2-(N-Ethyl-spiro-3'-pyrrolidinone)-2,3-dihydrothieno[2,3-b]thiophene-1,1-dioxide (4.3 g, 0.158 mol) in THF (150 mL) was stirred under nitrogen and borane-dimethyl sulfide complex (15.8 mL, 10M, 0.158 mol) added at room temperature. The resulting clear solution was heated to reflux under nitrogen for 48 hours. The reaction was cooled to room temperature and the volatiles removed in vacuo. The residue was partitioned between ethyl acetate and 3N HCl. The aqueous phase was extracted three times with ethyl acetate prior to adjusting the pH to 9.5. The slightly basic solution was extracted two times with ethyl acetate, and the combined organic extracts washed with saturated brine and dried over magnesium sulfate. Filtration and concentration in vacuo gave the title compound as a crystalline solid (3.1 g).

Step F: Preparation of 5-(N-ethyl-spiro-3'-pyrrolidine)-4,5-dihydrothieno[2,3-b]thiophene-2-sulfonamide-6,6-dioxide hydrochloride

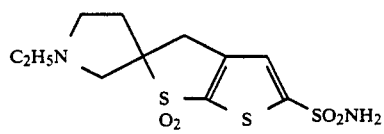

A solution of 2-(N-ethyl-spiro-3'-pyrrolidine)-2,3-dihydrothieno[2,3-b]thiophene-1,1-dioxide (3.0 g, 0.0116 mol) in dry THF was cooled to −78° C. under nitrogen. n-Butyllithium in hexane (5.6 mL, 2.5M) was added dropwise via syringe, the reaction becoming dark reddish-brown towards the end of the addition. After 40 minutes at −78° C., sulfur dioxide was condensed into the reaction mixture over a period of 10 minutes with the sulfinate precipitating as soon as it is formed. The reaction was warmed to room temperature, and the volatile components removed in vacuo. The residue was dissolved in an aqueous solution of sodium acetate (3.44 g, 0.042 mol) and hydroxylamine-O-sulfonic acid (4.7 g, 0.042 mol) and stirred overnight at room temperature. The aqueous phase was extracted with ethyl acetate while at low pH (<1), then made slightly alkaline (pH 8) and extracted again with ethyl acetate three times. The combined organic extracts were washed with brine, dried over magnesium sulfate, filtered and concentrated to provide the free base of the title compound as a foam (1.4 g). The free base was dissolved in methanol and treated with HCl. The methanol was evaporated and the resulting solid dried in vacuo to give the title compound mp=167° C. (foams). Anal. Calc. for $C_{14}H_{16}N_2O_4S_3 \cdot HCl \cdot 1/2H_2O$: C, 34.59; H, 4.74; N, 7.34. Found: C, 34.38; H, 4.96; N, 7.40.

Employing the procedures substantially as described in Example 10, Steps A through F but using an amine of formula $R^3H_2N$ in place of ethylamine in Step B, there are produced the spiro compounds described in Table III.

TABLE III

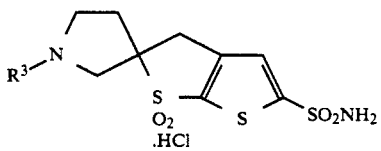

| R³ | mp (°C.) |
|---|---|
| i-C₄H₉ | 129-132 |
| CH₃ | 267-269 |
| CH₃OCH₂CH₂ | 98 |

EXAMPLE 11

2-Methyl-N-(4-morpholinoethyl)-6,6-dioxo-5-sulfamoyl-2,3-dihydrothieno[2,3-b]thiophene-2-carboxamide hydrochloride

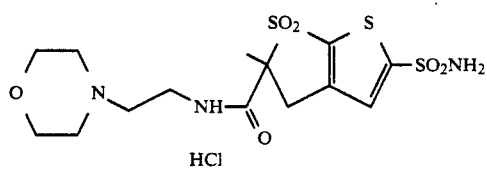

The title compound was prepared in the same way as N-[α-(S)-methoxycarbonyl-α-(4-hydroxyphenethyl)]-2-methyl-1,1-dioxo-5-sulfamoyl-2,3-dihydrothieno[2,3-b]thiophene-2-carboxamide (Example 9, Step F Alternate). Thus 2-methyl-1,1-dioxo-5-sulfamoyl-2,3-dihydrothieno[2,3-b]thiophene-2-carboxylic acid (0.80 g, 2.57 mmol) reacted with 4-morpholino-ethylamine (1.6 g, 12.65 mmol) to give the free base of the title compound (0.56 g). The free base was converted to the hydrochloride salt with methanolic HCl to give after drying 0.6 g (51% yield) of the title compound, mp=151°-153° C.

Anal. Calc'd. for $C_{14}H_{21}N_3O_6S_3$ HCl: C, 36.56; H, 4.82; N, 9.13. Found: C, 36.79; H, 4.85; N, 9.08.

EXAMPLE 12

(4-Morpholinoethyl)-2-methyl-6,6-dioxo-5-sulfamoyl-2,3-dihydrothieno[2,3-b]thiophene-2-carboxylate hydrochloride

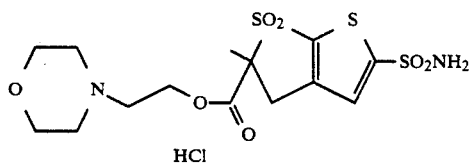

The title compound was prepared in the same way as N-[α-(S)-methoxycarbonyl-α-(4-hydroxyphenethyl)]-2-methyl-1,1-dioxo-5-sulfamoyl-2,3-dihydrothieno[2,3-b]thiophene-2-carboxamide (Example 9, Step F Alternate). Thus 2-methyl-1,1-dioxo-5-sulfamoyl-2,3-dihydrothieno[2,3-b]thiophene-2-carboxylic acid (1.0 g, 3.2 mmol) reacted with 4-morpholino-ethyl-alcohol (4.19 g, 32 mmol) to give the free base of the title compound (0.800 g). The free base was chromatographed with chloroform and 5% methanol to give 0.35 g. This was then converted to the hydrochloride salt with methanolic HCl to give after drying 0.375 g (25% yield) of the title compound, mp=110°-113° C.

Anal. Calc'd. for $C_{14}H_{20}N_2O_7S_3$ HCl: C, 36.47; H, 4.60; N, 6.08. Found: C, 36.23; H, 4.70; N, 6.11.

EXAMPLE 13

(Dimethylaminoethyl)-2-Methyl-6,6-dioxo-5-sulfamoyl-2,3-dihydrothieno[2,3-b]thiophene-2-carboxylate hydrochloride

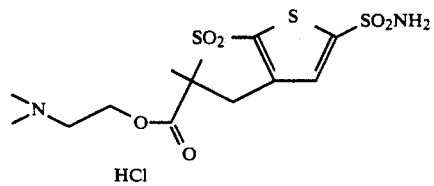

The title compound was prepared by suspending 2-methyl-1,1-dioxo-5-sulfamoyl-2,3-dihydrothieno[2,3-b]thiophene-2-carboxylic acid (1.0 g, 3.2 mmol) in thionyl chloride (5 ml) and THF (10 ml). This solution was then refluxed for five hours, afterwhich time the volatiles were removed in vacuo. The residue was dissolved in dry THF and added to a solution of dimethylaminoethanol at room temperature. After stirring for fifteen minutes the solvents were removed and the residue was partitioned between water and ethyl acetate. The aqueous layer was separated and extracted one more time. The combined extracts were washed with saturated sodium bicarbonate, and brine then dried over anhydrous sodium sulfate. Filtration and solvent removal left 600 mg of product. The free base was chromatographed with chloroform and 5% methanol to give a foam. This was then converted to the hydrochloride salt with methanolic HCl to give after drying 0.350 g (26% yield) of the title compound, mp=190°-194° C.

Anal. Calc'd. for $C_{12}H_{18}N_2O_6S_3$ HCl: C, 34.40; H, 4.56; N, 6.69. Found: C, 34.66; H, 4.52; N, 6.38.

EXAMPLE 14

(R)-(-)-2-Methyl-N-(4-imidazolyl-2-ethyl)-6,6-dioxo-5-sulfamoyl-2,3-dihydrothieno[2,3-b]thiophene-2-carboxamide hydrochloride

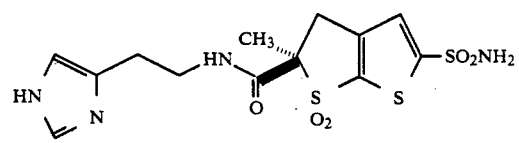

The title compound was prepared from histidine following the general procedure outlined in Example 11 for the synthesis of 2-methyl-N-(4-morpholino-2-ethyl)-6,6-dioxo-5-sulfamoyl-2,3-dihydrothieno[2,3-b]thiophene-2-carboxamide hydrochloride. The title compound melted at 110° C. and $[\alpha]_D^{20} = -78°$ (c=0.86, CH₃OH).

EXAMPLE 15

Eye Drop Formulation

| | | |
|---|---|---|
| 4,5-Dihydro-5-N,N-dimethyl-aminomethyl-5-methylthieno-[2,3-b]-thiophene-2-sulfon-amide-6,6-dioxide | 1 mg | 15 mg |
| Monobasic sodium phosphate 2H₂O | 9.38 mg | 6.10 mg |
| Dibasic sodium phosphate .12H₂O | 28.48 mg | 16.80 mg |
| Benzalkonium chloride | 0.10 mg | 0.10 mg |

| -continued | | |
|---|---|---|
| Water for injection q.s. and. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 16

Ophthalmic Ointment Formulation

| | |
|---|---|
| 5-Diethylamino-4,5-dihydro-5-methylthieno [2,3-b]-thiophene-2-sulfonamide-6,6-dioxide hydrochloride | 5 mg |
| petrolatum q.s. and. | 1 gram |

The compound and the petrolatum are aseptically combined.

EXAMPLE 17

Ophthalmic Insert Formulation

| | |
|---|---|
| 4,5-Dihydro-5-methyl-5-pyrrolidinomethylthieno-[2.3-b]thiophene-2-sulfonamide-6,6-dioxide hydrochloride | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate are then autocalved at 250° F. for ½ hour.

What is claimed is:

1. A compound of structural formula:

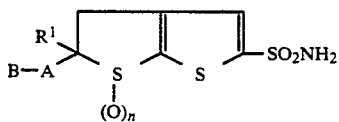

as the (R) or (S) enantiomer or mixtures thereof or an ophthalmologically acceptable salt thereof wherein:
n is 0, 1 or 2;

$R^1$ is
1) hydrogen
2) $C_{1-6}$ alkyl, or
3) $C_{2-6}$ alkenyl;
A is —$CH_2$— or —CO—;
B is —$OR^6$ or —$NR^2R^3$ wherein
$R^2$ is hydrogen or $C_{1-6}$alkyl;
$R^3$ is hydrogen, or $R^6$;
$R^6$ is
1) $C_{1-6}$alkyl,
2) $C_{2-6}$alkenyl,
3) $C_{2-6}$alkynyl,
4) $C_{1-6}$alkoxy-$C_{1-6}$alkyl or
5) $C_{1-6}$alkylthio-$C_{1-6}$alkyl or
6) $R^4R^5N$-$C_{2-6}$alkyl wherein $R^4$ and $R^5$ are independently hydrogen or $C_{1-6}$alkyl or joined together represent with the nitrogen to which they are attached, a 5-7 membered heterocycle comprising up to one additional hetero atom selected from O, S and N.

2. The compound of claim 1, wherein n is 2.

3. The compound of claim 2, wherein -A-B is —$CH_2NR^2R^3$.

4. The compound of claim 3, wherein $R^1$ is —$CH_3$, —$C_2H_5$ or —$C_3H_7$.

5. The compound of claim 4 which is:
4,5-dihydro-5-N,N-dimethylaminomethyl-5-methyl-thieno[2,3-b]thiophene-2-sulfonamide-6,6-dioxide;
5-diethylamino-4,5-dihydro-5-methylthieno[2,3-b]thiophene-2-sulfonamide-6,6-dioxide;
4,5-dihydro-5-methyl-5-pyrrolidinomethylthieno[2,3-b]thiophene-2-sulfonamide-6,6-dioxide;
5-(N-isobutylaminomethyl)-4,5-dihydro-5-methyl-thieno[2,3-b]thiophene-2-sulfonamide-6,6-dioxide;
5-(N-ethylaminomethyl)-4,5-dihydro-5-methyl-thieno[2,3-b]thiophene-2-sulfonamide-6,6-dioxide;
4,5-dihydro-5-ethoxyethylaminomethyl-5-methyl-thieno[2,3-b]-thiophene-2-sulfonamide-6,6-dioxide;
4,5-dihydro-5-methyl-5-isopropylaminomethyl-thieno[2,3-b]thiophene-2-sulfonamide-6,6-dioxide; or
4,5-dihydro-5-N,N-dimethylaminomethyl-5-n-propyl-thieno[2,3-b]thiophene-2-sulfonamide-6,6-dioxide;
(R)-(−)-2-Methyl-N-(4-imidazolyl-2-ethyl)-1,1-dioxo-5-sulfamoyl-2,3-dihydrothieno[2,3-b]thiophene-2-carboxamide, or an ophthalmologically acceptable salt thereof.

6. The R-enantiomer of the compound of claim 5.

7. An ophthalmological formulation for treating ocular hypertension and glaucoma comprising an ophthalmological carrier and an effective ocular antihypertensive and antiglaucoma amount of the compound of claim 1.

8. A method of treating ocular hypertension and glaucoma which comprises the topical ocular administration to a patient in need of such treatment of an effective ocular antihypertensive and antiglaucoma amount of the compound of claim 1.

* * * * *